US012650418B2

(12) United States Patent
Xia

(10) Patent No.: US 12,650,418 B2
(45) Date of Patent: Jun. 9, 2026

(54) WATER MONITORING WITH SOLID STATE NANOPORES

(71) Applicant: Goeppert, LLC, Philadelphia, PA (US)

(72) Inventor: Zehui Xia, Philadelphia, PA (US)

(73) Assignee: Goeppert, LLC, Philadelphia, PA (US)

( * ) Notice: Subject to any disclaimer, the term of this patent is extended or adjusted under 35 U.S.C. 154(b) by 441 days.

(21) Appl. No.: 18/220,521

(22) Filed: Jul. 11, 2023

(65) Prior Publication Data

US 2025/0020623 A1     Jan. 16, 2025

(51) Int. Cl.
*G01N 33/18* (2006.01)

(52) U.S. Cl.
CPC ................................. *G01N 33/1813* (2013.01)

(58) Field of Classification Search
CPC ........... G01N 33/1813; G01N 27/3272; G01N 33/48721; G01N 33/54326; G01N 33/5438; G01N 27/3271; G01N 33/48707; G01N 2021/6482; G01N 2021/825; G01N 2458/10
See application file for complete search history.

(56) References Cited

U.S. PATENT DOCUMENTS 11,598,012 B2 * 3/2023 Voskian ................. C25B 11/095
2018/0275088 A1 * 9/2018 Huff ..................... B01L 3/50273

FOREIGN PATENT DOCUMENTS

| CN | 105087791 A | * | 11/2015 | ........... C12Q 1/6816 |
| EP | 4177606 A1 | * | 5/2023 | ....... G01N 33/48721 |
| JP | 2004294422 A | * | 10/2004 | |

OTHER PUBLICATIONS

Wen et al., "A Sensitive and Label-Free Pb(II) Fluorescence Sensor Based on a DNAzyme Controlled G-Quadruplex/Thioflavin T Conformation", Dec. 16, 2016, Sensors, 16, 2155. (Year: 2016).*
Straub, John E., II, et al., "International Space Station Portable Water Characterization for 2013", 44th International Conference on Environmental Systems, Tucson, Arizona, Jul. 13-17, 2014.

(Continued)

*Primary Examiner* — Jennifer Wecker
*Assistant Examiner* — Tracy Ching-Tian Colena
(74) *Attorney, Agent, or Firm* — CM Law LLP; Michael P. Dunnam

(57) ABSTRACT

A solid-state nanopore system includes a single-molecule chip that works on the principle of pore occlusion by the detected molecule, which then can be registered as a change in ionic current. Low-noise and low-capacitance glass chips are used with ultrathin (<20 nm) silicon nitride (SiN) nanopores of 1.5-5 nm diameter and a miniaturized nanopore reader are used as the nanopore sensor, which is capable of sensing the presence of mercury ion ($Hg^{2+}$) and lead ion ($Pb^{2+}$) at concentrations down to 0.5 nM and 5 nM, respectively. Detectable distinct electrical translocation characteristics between the two metal ions were enabled by short DNA molecules (aptamers) functioning as a carrier, binding via specific interactions with the metal ions to provide a selective nanopore sensor for water monitoring by identification of electrical fingerprints of the respective ions.

14 Claims, 13 Drawing Sheets

(56)                References Cited

OTHER PUBLICATIONS

Surwade, Sumedh P., et al., "Water Desalination Using Nanoporous Single-Layer Graphene", Nature Nanotechnology, vol. 10, Issue 5, May 2015, (online: Mar. 23, 2015), pp. 459-464.

The Nanopore Site, https://www.thenanoporesite.com/nanopore-companies, printed on Oct. 3, 2025.

Thiruraman, Jothi Priyanka, et al., "Ions and Water Dancing Through Atom-Scale Holes: A Perspective Toward "Size Zero"", ACS Nano, vol. 14, Issue 4, Mar. 20, 2020, pp. 3736-3746.

Thiruraman, Jothi Priyanka, et al., "Stochastic Ionic Transport in Single Atomic Zero-Dimensional Pores", ACS Nano, vol. 14 Issue 9, Aug. 11, 2020, pp. 11831-11845.

Uram, Jeffrey D., et al., "Submicrometer Pore-Based Characterization and Quantification of Antibody-Virus Interactions", Nano Micro Small, vol. 2, No. 8-9, Aug. 2006, pp. 967-972.

Venta, Kimberly, et al., "Differentiation of Short, Single-Stranded DNA Homopolymers in Solid-State Nanopores", ACS Nano, vol. 7, Issue 5, Apr. 26, 2013, pp. 4629.4636.

Wang, Guihua, et al., "Nanopore Detection of Copper Ions Using a Polyhistidine Probe", Biosensors and Bioelectronics, vol. 53, Mar. 15, 2014, pp. 453.458.

Wang, Guihua, et al., "Probing Mercury (II)—DNA Interactions by Nanopore Stochastic Sensing", The Journal of Physical Chemistry B, vol. 117, Issue 17, Apr. 8, 2013, pp. 4763-4769.

Wanunu, Meni, "Nanopores: A Journey Towards DNA Sequencing", Physics of Life Reviews, vol. 9, Issue 2, Jun. 2012, pp. 125-158.

Wanunu, Meni, et al., "Discrimination of Methylcytosine from Hydroxymethylcytosine in DNA Molecules", Journal of the American Chemical Society, vol. 133, Issue 3, Jan. 26, 2011 (online: Dec. 14, 2010), pp. 486-492.

Wanunu, Meni, et al., "Nanopore Analysis of Individual RNA/Antibiotic Complexes", ACS Nano, vol. 5, No. 12, Nov. 8, 2011, pp. 9345-9353.

Wanunu, Meni, et al., "Rapid Electronic Detection of Probe-Specific microRNAs Using Thin Nanopore Sensors", Nature Nanotechnology, vol. 5, No. 11, Nov. 2010 (online: Oct. 24, 2010), pp. 807-814.

Wei, Ruoshan, et al., "Stochastic Sensing of Proteins with Receptor-Modified Solid-State Nanopores", Nature Nanotechnology, vol. 7, No. 4, Apr. 2012 (online: Mar. 11, 2012). pp. 257-263.

Wen, Shuang, et al., "Highly Sensitive and Selective DNA-Based Detection of Mercury(II) with a-Hemolysin Nanopore", Journal of the American Chemical Society, vol. 133, Issue 45, Oct. 13, 2011, pp. 18312-18317.

Wu, Yuangen, et al., "Selection of a DNA Aptamer for Cadmium Detection Based on Cationic Polymer Mediated Aggregation of Gold Nanoparticles", Analyst, vol. 139, Issue 6, Mar. 21, 2014 (online: Dec. 16, 2013), pp. 1550-1561.

Xia, Zehui, et al., "Deoxyribonucleic Acid Extraction from Mars Analog Soils and Their Characterization with Solid-State Nanopores", Astrobiology, vol. 22, No. 8, Aug. 2022 (online: Jul. 25, 2022), pp. 992-1008.

Xia, Zehui, et al., "New-Generation Spacecraft Water Monitoring With Flight-Ready Solid State Nanopores", 51st International Conference on Environmental Systems, Jul. 10-14, 2022.

Xia, Zehui, et al., "Protein-Enabled Detection of Ibuprofen and Sulfamethoxazole Using Solid-State Nanopores", Proteomics and Systems Biology, vol. 22, Issue 5-6, Mar. 22, 2022 (online: Jan. 2, 2022).

Xia, Zehui, et al., Spacecraft Water Analysis with Nanopore (SWAN), 53rd International Conference on Environmental Systems, Jul. 21-25, 2024.

Xue, Liang, et al., "Solid-State Nanopores Sensors", Nature Reviews Materials, vol. 5, No., Dec. 2020 (online: Sep. 21, 2020), pp. 931-951.

Zhmud, B.V., "Influence of Chemical Pretreatment on the Surface Properties of Silicon Nitride Powder", Colloids and Surfaces A: Physicochemical and Engineering Aspects, vol. 158, Issue 3, Nov. 1999, pp. 327-341.

Acar, Elif Turker, et al., "Biomimetic Potassium-Selective Nanopores", Science Advances, vol. 5, Issue 2, Feb. 8, 2019.

Akeson, Mark, et al., "Microsecond Time-Scale Discrimination Among Polycytidylic Acid, Polyadenylic Acid, and Polyuridylic Acid as Homopolymers or as Segments Within Single RNA Molecules", Biophysical Journal, vol. 77, Issue 6, Dec. 1999, pp. 3227-3233.

Amaya-González, Sonia, et al., "Aptamer-Based Analysis: A Promising Alternative for Food Safety Control", Sensors, vol. 13, Issue 12, Nov. 28, 2013, pp. 16292-16311.

Balan, Adrian, et al., "Improving Signal-to-Noise Performance for DNA Translocation in Solid-State Nanopores at MHz Bandwidths", Nano Letters, vol. 14, Issue 12, Dec. 2014, pp. 7215-7220.

Balan, Adrian, et al., "Suspended Solid-State Membranes on Glass Chips with Sub 1-pF Capacitance for Biomolecule Sensing Applications", Scientific Reports, vol. 5, Article No. 17775, Dec. 8, 2015.

Bandara, Y.M. Nuwan D.Y., et al., "Chemically Functionalizing Controlled Dielectric Breakdown Silicon Nitride Nanopores by Direct Photohydrosilylation", ACS Applied Materials and Interfaces, vol. 11, Issue 33, Jul. 26, 2019, pp. 30411-30420.

Bhattacharyya, Debmalya, et al., "Metal Cations in G-Quadruplex Folding and Stability", Frontiers in Chemistry, vol. 4, Article 38, Sep. 9, 2016.

Bock, James J., et al., "Silicon Nitride Micromesh Bolometer Arrays for SPIE", Proceedings of SPIE, Astronomical Telescopes and Instrumentation, Kona, HI, Jul. 31, 1998.

Branton, Daniel, et al., "The Potential and Challenges of Nanopore Sequencing", Nature Biotechnology, vol. 26, No. 10, Oct. 2008, pp. 1146-1153.

Briggs, Kyle, et al., "Kinetics of Nanopore Fabrication During Controlled Breakdown of Dielectric Membranes in Solution", Nanotechnology, vol. 26, Feb. 4, 2015.

Chakraborty, I., et al., "MEMS Micro-Valve for Space Applications", Institute of Electrical Engineers of Japan, Transducers, Sendai, Japan, Jun. 7, 1999 (revised Feb. 7, 2022).

Chien, Chen-Chi, et al., "Single-Stranded DNA Translocation Recordings Through Solid-State Nanopores on Glass Chips at 10 MHz Measurement Bandwidth", ACS Nano, vol. 13, Issue 9, Aug. 26, 2019 (web), pp. 10545-10554.

Chou, Yung-Chien, et al., "Lifetime and Stability of Silicon Nitride Nanopores and Nanopore Arrays for Ionic Measurements", ACS Nano, vol. 14, Issue 6, Apr. 10, 2020, pp. 6715-6728.

Chuang, Wen-Hsien, et al., "Mechanical Property Characterization of LPCVD Silicon Nitride Thin Films ant Cryogenic Temperatures", Journal of MIcroelectromechanical Systems, vol. 13, No. 5, Oct. 2004, pp. 870-879.

Cohen-Tanugi, David, et al., "Water Desalination Across Nanoporous Graphene", Nano Letters, vol. 12, Issue 7, Jun. 5, 2012, pp. 3602-3608.

Danda, Gopinath, et al., "Two-Dimensional Nanopores and Nanoporous Membranes for Ion and Molecule Transport", Manuscript, Feb. 1, 2019.

Das, Paul Masih, et al., "Centimeter-Scale Nanoporous 2D Membranes and Ion Transport: Porous MoS2 Monolayers in a Few-Layer Matrix", Nano Letters, vol. 19, Issue 1, Dec. 11, 2018, pp. 392-399.

Deamer, David W., et al., "Characterization of Nucleic Acids by Nanopore Analysis", Accounts of Chemical Research, vol. 35, No. 10, Sep. 27, 2002, pp. 817-825.

Deamer, David W., et al., "Nanopores and Nucleic Acids: Prospects for Ultrarapid Sequencing", Trends Biotechnol, vol. 18, Issue 4, Apr. 2000, pp. 147-151.

Deamer, David, et al., "Three Decades of Nanopore Sequencing", Nature Biotechnology, vol. 34, No. 5, May 2016, pp. 518-524.

EPA, "National Primary Drinking Water Regulations", EPA 816-F-09-004, May 2009.

Feng, Jiandong, et al., "Identification of Single Nucleotides in MoS2 Nanopores", Nature Nanotechnology, vol. 10, No. 12, Dec. 2015 (online: Sep. 21, 2015), pp. 1070-1076.

(56) References Cited

OTHER PUBLICATIONS

Feng, Jiandong, et al., "Observation of Ionic Coulomb Blockade in Nanopores", Nature Materials, vol. 15, Aug. 2016 (online: Mar. 28, 2016), pp. 850-855.

Fried, Jasper P., et al., "In Situ Solid-State Nanopore Fabrication", Royal Society of Chemistry, vol. 50, Feb. 24, 2021, pp. 4974-4992.

Garcia, Hector D., et al., "Establishment of Exposure Guidelines for Lead in Spacecraft Drinking Water", Aviation, Space, and Environmental Medicine, vol. 85, No. 7, Jul. 2014, pp. 715-720.

Gu, Li-Qun, et al., "Single Molecule Sensing by Nanopores and Nanopore Devices", National Institute of Health Public Access, Author Manuscript, Dec. 23, 2010.

Jain, Tarun, et al., "Heterogeneous Sub-Continuum Ionic Transport in Statistically Isolated Graphene Nanopores", Nature Nanotechnology, vol. 10, Dec. 2015 (online: Oct. 5, 2015), pp. 1053-1057.

Kasianowicz, John J., et al., "Characterization of Individual Polynucleotide Molecules Using a Membrane Channel", Proceedings of the National Academy of Sciences, vol. 93, No. 24, Nov. 26, 1996, pp. 13770-13773.

Kim, Mina, et al., "Arsenic Removal from Vietnamese Groundwater Using the Arsenic-Binding DNA Aptamer", Environmental Science & Technology, vol. 43, No. 24, Nov. 12, 2009, pp. 9335-9340.

Kong, Jinglin, et al., "Specific Biosensing Using DNA Aptamers and Nanopores", Advanced Functional Materials, vol. 29, No. 3, Jan. 17, 2019, 1807555 (6 pages).

Kwok, Harold, et al., "Nanopore Fabrication by Controlled Dielectric Breakdown", PLOS One, vol. 9, Issue 3, Mar. 21, 2014.

Lerner, Leticia Koch, et al., "Replication of G Quadruplex DNA", Genes, vol. 10, Issue 2, Jan. 29, 2019.

Lin, Kabin, et al., "Surface Charge Density Inside a Silicon Nitride Nanopore", Langmuir, vol. 37, Issue 35, Aug. 4, 2021, pp. 10521-10528.

Lin, Zhenzhen, et al., "Impedimetric Immobilized DNA-Based Sensor for Simultaneous Detection of Pb2+, Ag+, and Hg2+", Analytical Chemistry, Jul. 28, 2011, pp. 6896-6901.

Martin, Lisa C., et al., "Thin Film Sensors for Surface Measurements", NASA/TM-2001-211149, 19th International Congress on Instrumentation in Aerospace Simulation Facilities, Cleveland, OH, Aug. 27-30, 2001.

Mayne, Laura,a et al., "The Design and Characterization of Multifunctional Aptamer Nanopore Sensors", ACS Nano, vol. 12, Issue 5, May 2, 2018, pp. 4844-4852.

Meller, Amit, et al., "Single Molecule Measurements of DNA Transport Through a Nanopore", Electrophoresis, vol. 23, Issue 16, Aug. 20, 2002, pp. 2583-2591.

Merchant, Christopher A., et al., "DNA Translocation Through Graphene Nanopores", Nano Letters, vol. 10, Issue 8, Jul. 23, 2010, pp. 2915-2921.

Mikolajick, Thomas, "The Influence of Surface Oxidation on the pH-Sensing Properties of Silicon Nitride", Sensors and Actuators B: Chemical, vol. 58, Issues 1-3, Sep. 21, 1999, pp. 450-455.

Niedzwiecki, David J., et al., "Detection of Single-Analyte and Environmental Samples with Silicon Nitride Nanopores: Antarctic Dirt Particulates and DNA in Artificial Seawater", Review of Scientific Instruments, vol. 91, Issue 3, Mar. 25, 2020.

Niedzwiecki, David J., et al., "Observing Changes in the Structure and Oligomerization State of a Helical Protein Dimer Using Solid-State Nanopores", ACS Nano, vol. 9, No. 9, Aug. 11, 2015, pp. 8907-8915.

O'Hern, Sean C., et al., "Selective Ionic Transport Through Tunable Subnanometer Pores in Single-Layer Graphene Membranes", Nano Letters, vol. 14, Issue 3, Feb. 3, 2014, pp. 1234-1241.

Rollings, Ryan C., et al., "Ion Selectivity of Graphene Nanopores", Nature Communications, vol. 7, Apr. 22, 2016.

Rosenstein, Jacob K., et al., "Integrated Nanopore Sensing Platform with Sub-Microsecond Temporal Resolution", Nature Methods, vol. 9, No. 5, May 2021, pp. 487-494.

Shekar, Siddharth, et al., "Measurement of DNA Translocation Dynamics in a Solid-State Nanopore at 100 ns Temporal Resolution", Nano Letters, vol. 16, Issue 7, Jun. 22, 2016, pp. 4483-4489.

Shreiner, R.H., et al., "Primary Standards and Standard Reference Materials for Electrolytic Conductivity", National Institute of Standards and Technology Special Publication 260-142, May 2004.

Sigel, Astrid, et al, "The Alkali Metal Ions: Their Role for Life", Metal Ions in Life Sciences, vol. 16, 2016.

Sint, Kyaw, et al, "Selective Ion Passage Through Functionalized Graphene Nanopores", Journal of the American Chemical Society, vol. 130, Issue 49, Nov. 14, 2008, pp. 16448-16449.

Smirnov, Ivan V., et al., "Pb EXAFS Studies on DNA Quadruplexes: Identification of Metal Ion Binding Site", Biochemistry, vol. 41, Issue 40, Sep. 7, 2002, pp. 12133-12139.

Storm, A.J., et al., "Fabrication of Solid-State Nanopores with Single-Nanometre Precision", Nature Materials, vol. 2, Issue 8, Aug. 2003 (online: Jul. 13, 2003), pp. 537-540.

* cited by examiner

WATER MONITORING WITH SOLID STATE NANOPORES

GOVERNMENT INTEREST

The subject matter described herein was developed with funding received under NASA Contract Number 80NSSC21C0368. NASA may have certain rights in the subject matter described herein.

TECHNICAL FIELD

Examples set forth herein generally relate to methods using a solid-state nanopore chip to sense metal ions such as mercury and lead ions and using short DNA molecules (aptamers) that bind with the metal ions to function as a carrier.

BACKGROUND

A solid-state nanopore is a nanoscale or larger hole (from a few nm to hundreds of nm) drilled into an inorganic-made plate, e.g., silicon nitride (SiN). SiN pores can withstand high temperatures and be sterilized to minimize contamination. In the early 1990s, nanopores were envisioned in the context of protein pores (alpha-hemolysin) by Kasianowicz et al., who used them to analyze individual polynucleotides. SiN nanopores were first fabricated by using electron and ion beam drilling. They are useful in biomolecular detection, and promising for new diagnostic and filtering devices. The simplest nanopore instrument contains an electrolytic solution separated by the pore. When voltage is applied, the ionic current flowing through the pore is measured (on the order of 0.1 nA to 1 nA). The modulation of current caused by the passage of a molecule through the pore reflects the physical and chemical properties (e.g., size, shape, charge), creating electrical "fingerprints" that may form a basis for quantitative detection. Nanopore diameters, materials, and properties can be fine-tuned using a range of techniques from electron irradiation to electroporation and down to single-atom-thin pores in a multitude of materials and sub-nm pore diameters. SiN pores can distinguish monomer and dimer proteins of only 33 amino acids long, analyze antibiotic/RNA complexes, identify the percentage of hydroxymethyl cytosine (hmC) nucleotide within a larger DNA strand, and distinguish between different DNA homopolymers and individual DNA nucleotides.

A solid-state nanopore based single-molecule detection instrument has been developed by the present inventors for the search of life in outer space, featured on the cover of the Review of Scientific Instruments (March 2020). This portable, cm-scale instrument relies on fast electronics (up to 200 kHz) and ultrathin (5-20 nm) solid-state nanopores in low-capacitance glass, and the platform works with a variety of sample formats (solid, liquid, etc.), dissolved in salt solutions for measurements. This platform has been used to detect and characterize proteins, mRNA, and DNA in artificial seawater and Mars analog soils, and small pharmaceutical molecules (~1 nm) in aqueous samples.

FIG. 1 shows schematics of a solid-state nanopore chip 10 developed by the present inventors for measuring ionic current flow through a solid-state hole ("nanopore"). As shown in FIG. 1A, in the absence of the particle in the electrolytic solution separated by the pore 12, the ionic current signal is constant with a root-mean-square (rms) noise, $I_{rms}$, that mostly depends on the chip capacitance and instrument specifications. As shown in FIG. 1B, the modulation of the current caused by the passage of the molecule 14 through the pore 12 creates a current pulse or "fingerprint" that forms a basis for quantitative detection. FIG. 1C illustrates a Transmission Electron Microscope (TEM) image of a 20 nm-thickness SiN nanopore. FIG. 1D illustrates a sample nanopore detection instrument disclosed by the present inventors including the low-noise nanopore chip (e.g., $5 \times 5 \times 0.2$ mm$^3$) 10 inserted into a fluidic cell 16. The fluidic cell (e.g., $25 \times 15 \times 5$ mm$^3$) 16 with microfluidic channels forming reservoirs in contact with the nanopore chip 10 is inserted into the portable nanopore reader (e.g., $10 \times 4.5 \times 2$ cm$^3$) 18 for detection.

While solid-state nanopores have been used to detect a wide range of organic molecules, the topic of sensing metal ions remains a less explored yet very important field. Existing analytical techniques, mostly based on mass spectroscopy, have the limitation of long sample preparation, high cost, and high level of required expertise.

To date, a solid-state nanopore chip 10 of the type used in the configuration shown in FIG. 1D has not been commercially available and thus has not been used for applications such as sensing metal ions in water. To implement solid-state nanopores for sensing metal ions in water, several technical restrictions have had to be overcome. For example, freely suspended and robust silicon nitride membranes less than 20 nm thick and without holes has proven to be problematic. Also, there has been no widely available technique for making a solid-state nanopore, selecting chips including the solid-state nanopore, and then treating (e.g., cleaning) the solid-state nanopore. In addition, there has been no established fluidic cell for holding solid-state nanopores for water treatment applications. For at least these reasons, the state of the art has been limited to the use of much larger polymer nanopores (e.g., 800 nm diameter) to measure mercury and lead ion concentrations in a fluid by enhancing the signal measurement through modification of a nanoparticle so that an aptamer having a strong binding affinity with lead or mercury ions will bind to the nanoparticle. However, the polymer nanopores are not robust enough for use in space, and the nanoparticles have diameters of 150-200 nm that are too large to be used with solid-state nanopores.

SUMMARY

Various examples are now described to introduce a selection of concepts in a simplified form that are further described below in the Detailed Description. The Summary is not intended to be used to limit the scope of the claimed subject matter.

Sample configurations described herein relate to a method of sensing a metal ion in a fluid (e.g., water). The method has application for testing water aboard a spacecraft. The method includes inserting a solid-state nanopore chip having at least one nanopore of less than 20 nm diameter into a fluidic cell. A fluid is provided into the fluidic cell that includes an aptamer having a strong binding affinity with the metal ion to form a carrier. The concentration of the carrier is measured as the fluid passes through the at least one nanopore of the solid-state nanopore chip. For example, the concentration of the carrier may be determined by recording translocation events of carrier molecules one at a time using a nanopore reader as the carrier molecules translocate through the at least one nanopore. In the sample configurations, the solid-state nanopore chip comprises silicon nitride (SiN) nanopores that are less than 20 nm thick and have a diameter of 1.5-5 nm.

Examples are provided for measuring a lead ion ($Pb^{2+}$) in the fluid. In such a case, the aptamer may comprise a guanine (G) rich aptamer that binds with a target lead ion to from a lead carrier. The resulting lead carrier has a quadruplex structure that is electronically detected by the solid-state nanopore chip as the lead carrier passes through the at least one nanopore. The lead ion may have concentrations as low as 5 nM in the fluid.

In other examples where the metal ion is a mercury ion ($Hg^{2+}$), the aptamer may comprise a thymine (T) rich aptamer that binds with a target mercury ion to form a mercury carrier. The mercury carrier may comprise T-Hg-T base pairs in a duplex hairpin structure that is electronically detected by the solid-state nanopore chip as the lead carrier passes through the at least one nanopore. The mercury ion may have concentrations as low as 0.5 nM in the fluid.

A water monitoring system is also described that is adapted to sense a metal ion in water. The system includes a fluidic cell that holds water comprising a concentration of an aptamer having a strong binding affinity with the metal ion to form a carrier. A solid-state nanopore chip that has at least one nanopore of less than 20 nm diameter is disposed in the fluidic cell for testing the water. A nanopore reader measures concentration of the carrier as the water passes through the at least one nanopore of the solid-state nanopore chip. The nanopore reader records translocation events of carrier molecules one at a time as the carrier molecules translocate through the at least one nanopore. The solid-state nanopore chip may comprise silicon nitride (SiN) nanopores that are less than 20 nm thick and have a diameter of 1.5-5 nm. The fluidic cell may be adapted for use on a spacecraft.

For detecting a lead ion, the aptamer may comprise a guanine rich aptamer that binds with a target lead ion to from a lead carrier. The lead carrier has a quadruplex structure that is electronically detected by the solid-state nanopore chip as the lead carrier passes through the at least one nanopore. On the other hand, for detecting a mercury ion, the aptamer may comprise a thymine rich aptamer that binds with a target mercury ion to form a mercury carrier. The mercury carrier may comprise T-Hg-T base pairs in a duplex hairpin structure that is electronically detected by the solid-state nanopore chip as the lead carrier passes through the at least one nanopore.

This summary section is provided to introduce aspects of the inventive subject matter in a simplified form, with further explanation of the inventive subject matter following in the text of the detailed description. The particular combination and order of elements listed in this summary section is not intended to provide limitation to the elements of the claimed subject matter. Rather, it will be understood that this section provides summarized examples of some of the embodiments described in the Detailed Description below.

BRIEF DESCRIPTION OF THE DRAWINGS

In the drawings, which are not necessarily drawn to scale, like numerals may describe similar components in different views. Some nonlimiting examples are illustrated in the figures of the accompanying drawings in which.

DETAILED DESCRIPTION

A detailed description of the methodology for sensing mercury and lead ions in water will be described with reference to FIGS. 2-8. Although this description provides a detailed description of possible implementations, it should be noted that these details are intended to be exemplary and in no way delimit the scope of the inventive subject matter.

Figure 1A:
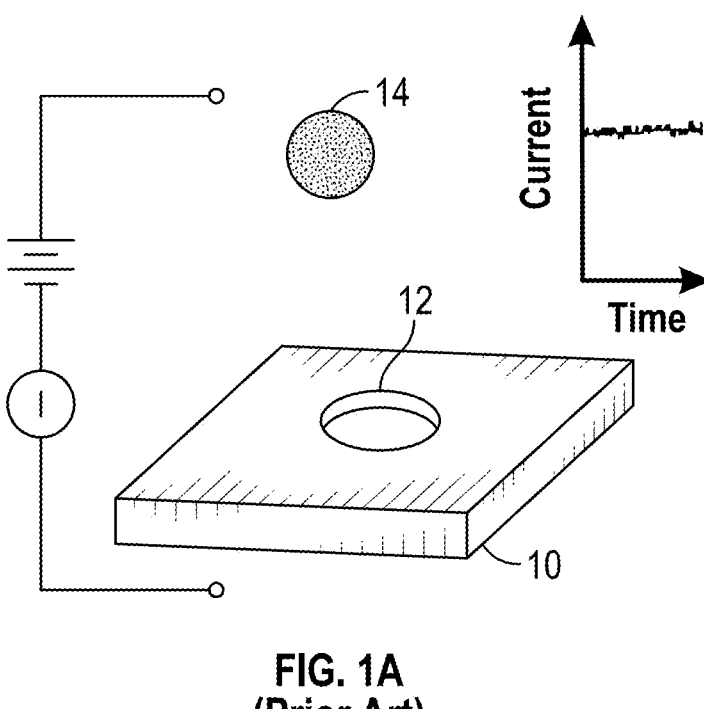
FIG. 1A is an illustration of a solid-state nanopore chip in the absence of a particle.
Figure 1B:
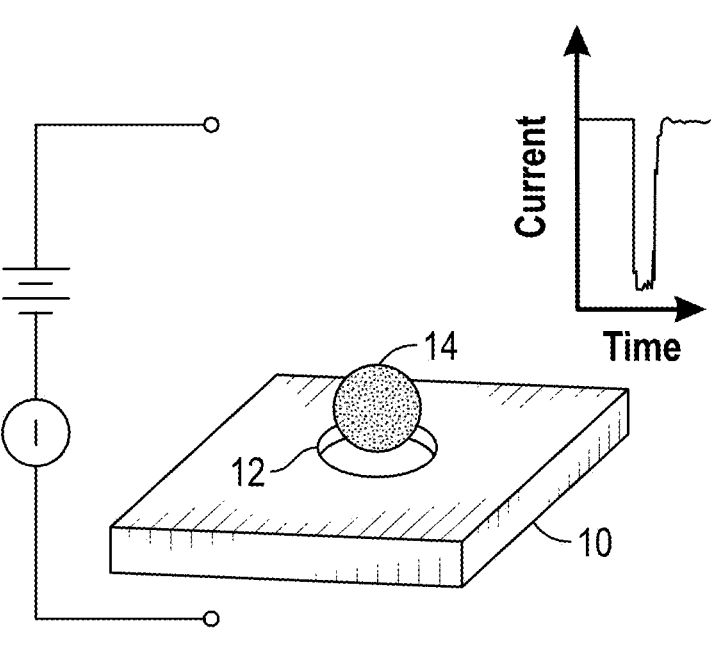
FIG. 1B is an illustration of the solid-state nanopore chip of FIG. 1A showing how the passage of a particle through the nanopore is detected as a current pulse.
Figure 1C:
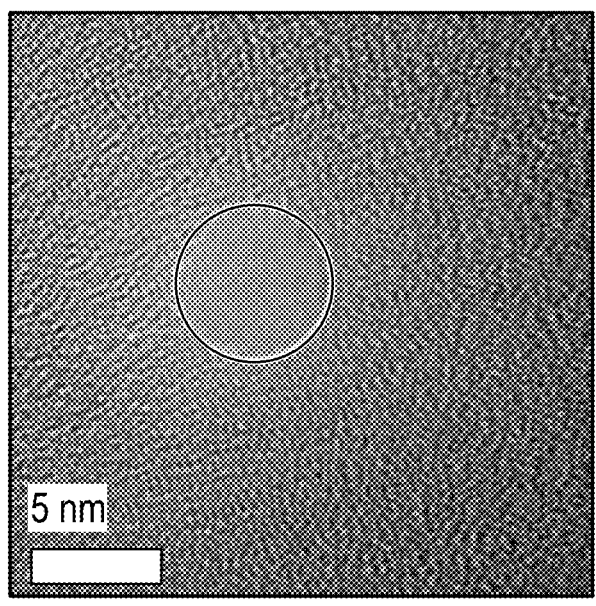
FIG. 1C is a Transmission Electron Microscope (TEM) image of a 20 nm thickness SiN nanopore.
Figure 1D:
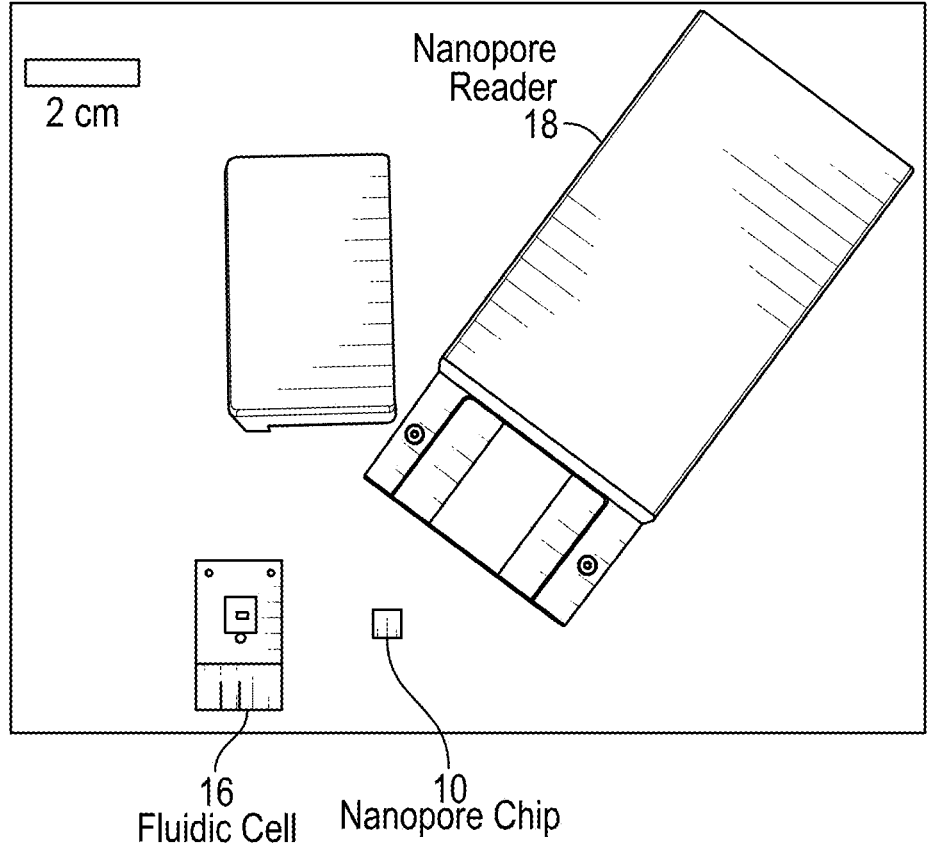
FIG. 1D illustrates a sample nanopore detection instrument including the solid-state nanopore chip of FIG. 1A, a fluidic cell, and a portable nanopore reader.

The following description relates to a modified version of the modular nanopore instrument of FIG. 1D that has tailored pore properties designed to detect selected inorganic ions for water monitoring purposes. In a sample configuration, the water monitoring system is designed for use in a spacecraft (e.g., the International Space Station (ISS)). The solid-state nanopore chip described herein features a powerful, portable, and easy-to-operate technique that enables the detection of small analytes (e.g., mercury ions ($Hg^{2+}$) and lead ions ($Pb^{2+}$)) within minutes. The solid-state nanopore system described herein is a single-molecule chip that works on the principle of pore occlusion by the detected molecule, which then can be registered as a change in ionic currentionic current. Low-noise and low-capacitance glass chips with ultrathin (<20 nm) SiN nanopores of 1.5-5 nm diameter and a miniaturized nanopore reader are used to sense the presence of mercury ions ($Hg^{2+}$) and lead ions ($Pb^{2+}$) at concentrations down to 0.5 nM and 5 nM, respectively, which are below the U.S. EPA maximum contaminant level (MCL) of 25 nM and Spacecraft Water Exposure Guidelines (SWEGs) of 43 nM. Distinguishable signals were observed for a range of concentrations from 0.5 nM to 5 µM for $Hg^{2+}$ and 5 nM to 5 µM for $Pb^{2+}$. It will be appreciated that it is desirable for the SiN nanopores to be as small as possible for optimal detection characteristics but large enough to allow passage of the mercury ions and lead ions. In sample configurations, the solid-state nanopore has a diameter of less than 20 nm and a preferred diameter of 1.5-5 nm that results in a decent percentage of pore blockage and optimized accuracy.

In sample configurations, the detection was enabled by short DNA molecules (aptamers) functioning as a carrier. The aptamers bind via specific interactions with the metal ions. Distinct electrical translocation characteristics between the lead and mercury metal ions were also observed, enabling a selective nanopore chip for water monitoring by identifying the respective "electrical fingerprints" of the lead and mercury ions.

In the sample application of a water monitoring system for use in a spacecraft such as the ISS, it is observed that such spacecraft provide a highly controlled, stable, and isolated environment. The current water monitoring capability in the ISS, for example, is limited to electrical conductivity (for inorganics), total organic carbon (for organics), and selected ions of iodine and silver (residual disinfectants). To detect other analytes in water, samples must be brought down to earth. The water quality and safety is designed into process hardware and a monitoring system (e.g., chips) can be imparted to make sure that hardware is operating normally. If there is a trigger indicating something is wrong, that means the quality could be degraded and the crew would have to do the troubleshooting. Thus, there is a strong demand for chips that need little calibration and that are simple to use and do not require significant crew time. The single-molecule nanopore chip described herein features minimal standard calibration and a quick turnaround time and may be operated by non-experts for monitoring water quality in the ISS and other crewed spacecrafts, as well as in other water quality monitoring applications on earth.

The analyte detection strategy described herein takes advantage of the specific interactions between analytes of interest and the recognition carrier molecules. This scheme helps to differentiate and to identify analytes of similar physiochemical properties (e.g., metal ions of the same valency, similar diameter, etc.). The translocation of a carrier with a bound analyte through the nanopore can be distinguished from that of the carrier alone based on the ionic current blockade. The presence of the analyte will 1) increase or decrease the number of translocation events, and/or 2) produce different current vs. time traces due to the interaction between analytes and carrier. The use of carrier provides a solution to detecting analytes substantially smaller than the nanopore. The larger diameter of the carrier-analyte complex can slow down the fast translocation of a small analyte through the nanopore and improve the signal-to-noise ratio which is often governed by the volume of the molecule. Furthermore, carriers usually have well-characterized physiochemical properties (e.g., diameter and charge) and enable the detection of particles that may not otherwise be passing through the pore at all. For example, when bovine serum albumin (BSA, diameter ~6-8 nm) was used previously as the carrier protein to detect small pharmaceutical molecules of ibuprofen and sulfamethoxazole (both with similar diameters of ~1-2 nm), changes in electrical signal characteristics (event durations, rates, current magnitudes and estimated particle diameters) of BSA-drug complexes were observed compared to BSA only, and differences were observed between these two small pharmaceuticals.

In the applications described herein, short single-stranded oligonucleotide "aptamers" with known sequences are used as a carrier to detect metal ions using a portable, easy-to-use solid-state nanopore chip. The metal ion-aptamer interactions have been observed to establish that specific DNA sequences have strong binding affinity with specific metal ions. Aptamers adopt different structures in the presence of a target metal ion, which results in the change of their properties and the signals that they produce when passing through the nanopores. For lead ion ($Pb^{2+}$) detection, guanine (G)-rich aptamers were chosen that can form the $Pb^{2+}$-stabilized G-quadruplex structure shown in FIG. 2 and FIG. 3.

Figure 2:
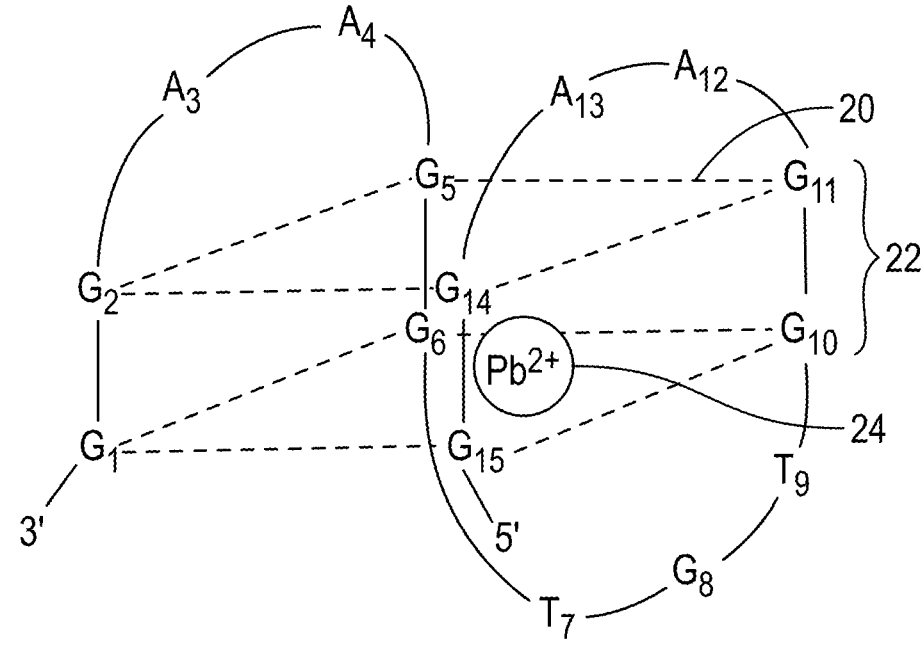
FIG. 2 is a schematic representation of the intramolecular G-quadruplex structures of a $Pb^{2+}$-specific aptamer.

FIG. 2 is a schematic representation of the intramolecular G-quadruplex structures of a $Pb^{2+}$-specific aptamer. As illustrated, four G bases can associate through Hoogsteen hydrogen bonding to form a square planar structure called a guanine tetrad (G-tetrad or G-quartet) 20 held together by G-G base pairs, and two or more guanine tetrads (from G-tracts, continuous runs of guanine) 20 can stack on top of each other to form a G-quadruplex cage 22. The G-quadruplex cage 22 is further stabilized by the presence of $Pb^{2+}$ ion 24, which sits in a central channel between each pair of tetrads 20. The lead ions 24 can coordinate tightly with the eight surrounding guanine oxygen atoms and position themselves between the two planes. In the illustrated case, one aptamer holds one lead ion within the G-quadruplex cage 22.

Figures 3A, 3B, 3C:
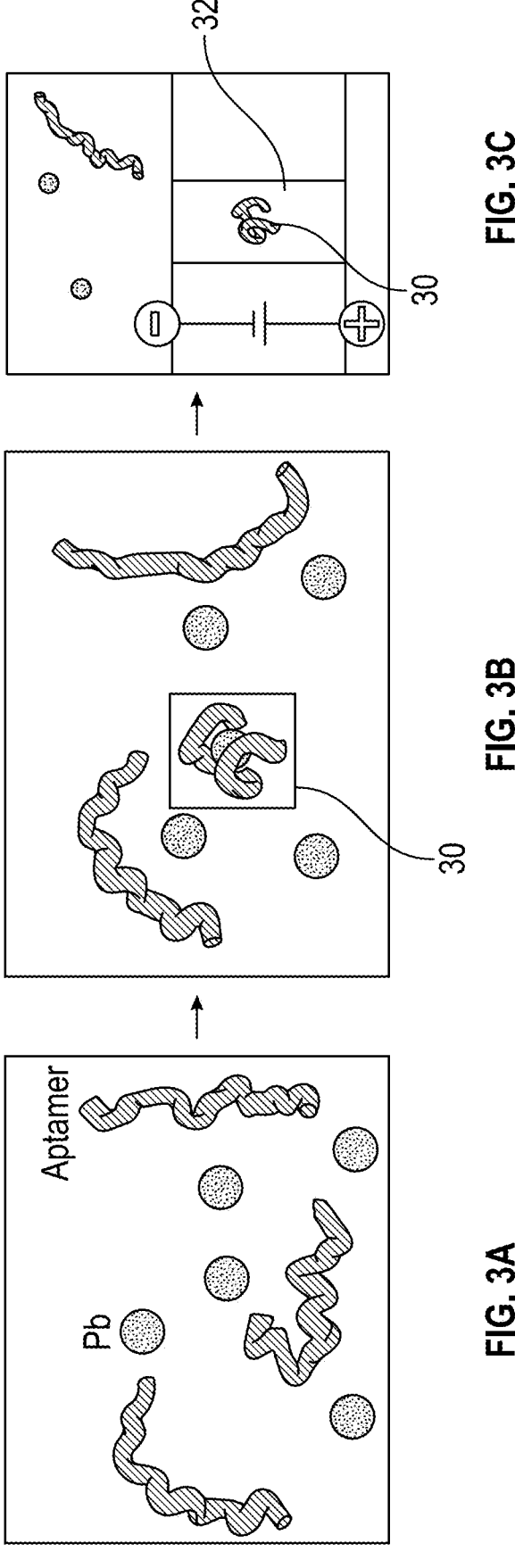
FIG. 3A is a schematic representation of a specific aptamer that binds with a target lead ion as a carrier.
FIG. 3B is a schematic representation showing that, upon binding, the aptamer of FIG. 3A will display a quadruplex structure.
FIG. 3C is a schematic representation showing the formed aptamer-$Pb^{2+}$ complex being electronically detected using a nanopore.

FIGS. 3A-3C illustrate a scheme of lead ion ($Pb^{2+}$) detection using aptamers as a carrier and 2 to 5 nm diameter SiN nanopores. FIG. 3A is a schematic representation of a specific Guanine-rich aptamer that binds with a target lead ion as a carrier, while FIG. 3B is a schematic representation showing that, upon binding, the aptamer of FIG. 3A will display a quadruplex structure 30. FIG. 3C is a schematic representation showing the formed aptamer-$Pb^{2+}$ complex structure 30 being electronically detected using a nanopore 32. Approximate dimensions of molecules in the scheme: aptamer is 1.1-1.3×5 $nm^2$ (diameter×length), $Pb^{2+}$ is 0.1 nm (diameter), and aptamer-$Pb^{2+}$ quadruplex structure is 2.6-2.8×1 $nm^2$ (diameter×length).

Figures 4A, 4B, 4C:
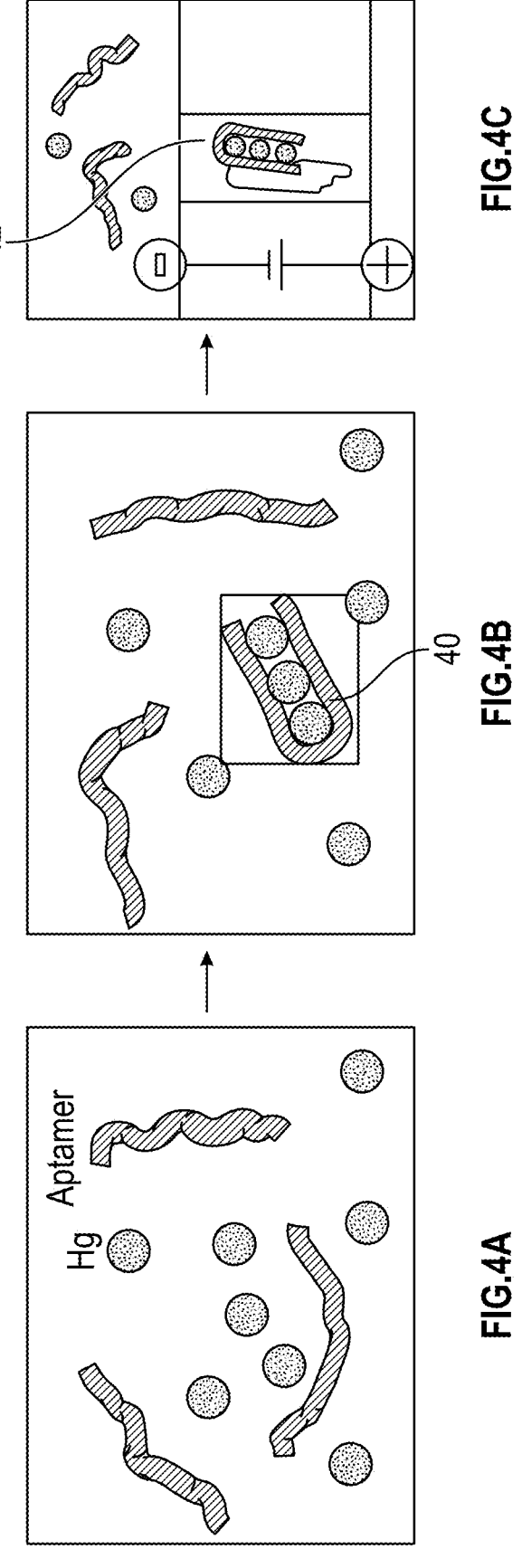
FIG. 4A is a schematic representation of a specific aptamer that binds with a target mercury ion as a carrier.
FIG. 4B is a schematic representation showing that, upon binding, the aptamer of FIG. 4A will display a duplex hairpin structure.
FIG. 4C is a schematic representation showing the formed aptamer-$Hg^{2+}$ complex being electronically detected using a nanopore.

On the other hand, FIGS. 4A-4C illustrate a scheme of mercury ion ($Hg^{2+}$) detection using aptamers as a carrier and 2 to 5 nm diameter SiN nanopores. For mercury ion ($Hg^{2+}$) detection, thymine (T)-rich aptamers (FIG. 4A) were used in which the T-T mismatches selectively capture $Hg^{2+}$ to form the T-Hg-T base pairs like a duplex hairpin structure 40 as shown in FIG. 4B. FIG. 4C is a schematic representation showing the formed aptamer-$Hg^{2+}$ complex 40 being electronically detected using a nanopore 42. Approximate dimensions of molecules in the scheme: aptamer is 1.1-1.3×

6.6 nm$^2$ (diameter×length), Hg$^{2+}$ is 0.1 nm (diameter), and aptamer-Hg$^{2+}$ hairpin structure is 2.2-2.6×3.3 nm$^2$ (diameter×length).

Such distinct electrical translocation characteristics (e.g., event rate, estimated diameters, and dwell time) can be sensed by small nanopores. For example, a SiN nanopore platform of the type shown in FIG. 1D may be adapted to sense the presence of Hg$^{2+}$ and Pb$^{2+}$ with the use of short aptamer carriers of the type shown in FIG. 3 and FIG. 4 (whose sequence is chosen to have preferential binding to desired metal ions at concentrations down to 0.5 nM for Hg$^{2+}$ and 5 nM for Pb$^{2+}$, which are below the U.S. EPA maximum contaminant level (MCL) of 25 nM (~2 μg/L) and Spacecraft Water Exposure Guidelines (SWEGs) of 43 nM (~9 μg/L). The use of such aptamers as carriers provides many opportunities and a large library of possible sequences to tune the aptamers by adjusting their structure with single nucleotide precision, which translates to tuning the aptamer-metal ion interactions and nanopore signals. Furthermore, the single-molecule nanopore instrument of FIG. 1D allows the detection of low-concentration metal ions in water and is thus a promising tool for a miniaturized analytical laboratory for future space missions.

Materials and Methods

The oligonucleotides used for the aptamers were purchased from Integrated DNA Technologies (IDT Inc., IA, USA). The sequence of aptamer used for Pb$^{2+}$ detection is a guanine-rich aptamer and the sequence for Hg$^{2+}$ is a thymine-rich aptamer. Lead (II) standard solution (1 mg/ml Pb in 2% HNO$_3$) and mercury (II) standard solution (1 mg/ml Hg in 10% HNO$_3$) were purchased from Thermo Scientific. All chemicals were prepared using Milli-Q (Millipore, Billerica, MA) water with a resistivity of 18.2 MΩ cm$^{-1}$. Experiments were conducted in 0.5 M KCl at pH 5. All stock solutions were stored at 4° C. and used within one week of initial preparation.

Nanopores were fabricated in 20 nm-thick, low-stress SiN membrane glass chips of the type illustrated in FIG. 1D. Pores were drilled with a 200 keV focused electron beam in a JEOL 2010F transmission electron microscope (TEM, JEOL USA Inc., USA). A TEM holder was used to hold the chip for drilling. It is noted that other nanopore fabrication methods including electroporation may improve the fabrication rate but lack the direct mapping of pore characteristics (e.g., shape, quantity, and location on the membrane). The diameters of the nanopore were measured by imaging right after drilling in vacuum. After pore drilling and prior to ionic measurement, chips were cleaned by UV/ozone treatment to aid pore wetting. The UV/ozone treatment was done by exposing the chip under the UV/ozone lamp (6 W, emission wavelengths of 254 and 185 nm) held approximately 5 cm above the chips for 1 hour 40 minutes on each side. After cleaning, the protonation/deprotonation of silanol and amine groups in the electrolyte solution make the surface negatively or positively charged and the surface properties of SiN depends on its preparation process. Chips were then either inserted in ionic solution for measurement or kept in isopropanol.

Nanopore chips were assembled in a fluidic cell 16 (FIG. 1D). The following samples were measured as they were driven through the pores at voltages of +100 to +400 mV: 1) the aptamer only as the first control sample, 2) metal ion only (Pb$^{2+}$ or Hg$^{2+}$) as the second control sample, and 3) aptamer-metal ion complexes (used for detecting metal ions). Buffer solutions containing aptamers were added to the cis-side of the nanopore for the first control measurement. These aptamer samples were prepared in buffer containing 0.5 M KCl at pH 5 in a final concentration of 50 nM. The trans-chamber was filled with the same buffer. The passage of aptamer across the pore caused a reduction of the current. The real time analyses of the electrical spikes provide a reference signal for the subsequent experiments with metal ions. In parallel, the aptamer was mixed with several concentrations (from 0.5 nM to 5 μM) of Pb$^{2+}$ or Hg$^{2+}$ and loaded to the same pore. As shown below, the binding of metal ions results in a new electrical fingerprint when compared to the control experiments without them.

A portable chip holder and a nanopore reader 18 (FIG. 1D) were used to record translocation events of molecules one at a time. The nanopore reader 18 supports a sampling rate up to 200 k samples/second. The data was analyzed using pCLAMP 10.3 (Molecular Devices, CA), with which the characteristic dwell time (duration of each translocation event) and the mean current blockade (magnitude of the ionic current reduction) were extracted. The data was further analyzed using OriginLab (OriginLab, MA). For each set of measurements, data was collected using the same nanopore to minimize possible influence from pore-to-pore variance unless significant pore expansion or clogging was observed. Nanopore chips were rinsed with DI water and isopropanol between each measurement to eliminate cross-contamination and restore a flat, baseline signal. The experiment was repeated using two nanopore chips for each experiment to confirm the trends reported.

Detection of Metal Ions without Using Aptamers as the Carrier

Using a ~1.8 nm diameter pore, not many current spikes caused by metal ions were observed. As shown in FIG. 5, there were less than 5 events above the threshold in a period of 80 seconds, indicating the undetectable translocation of either Pb$^{2+}$ or Hg$^{2+}$. The small nanopore chosen here was used to maximize the signal-to-noise ratio in order to realize the direct detection of metal ions. However, the ion current through the pore remained unchanged compared to the open pore current over a course of 80 seconds, indicating the unmeasurable electrical signals of Pb$^{2+}$ or Hg$^{2+}$. From Equation (1), the current blockage (ΔI) may be related to the pore diameter (d$_{pore}$):

$$\frac{\Delta I}{V_{bias}} = \sigma \left\{ \left( \frac{4t}{\pi d_{pore}^2} + \frac{1}{d_{pore}} \right)^{-1} - \left[ \frac{4t}{\pi \left( d_{pore}^2 - d_{particle}^2 \right)} + \frac{1}{\sqrt{d_{pore}^2 - d_{particle}^2}} \right]^{-1} \right\} \tag{1}$$

where t is the thickness of the pore and is 20 nm here, d$_{pore}$ is the calculated diameter of the pore, d$_{particle}$ is the diameter of the translocating particle, A/is the current blockade, V$_{bias}$ is the applied transmembrane voltage, and σ is the ionic solution conductivity (σ~12 S/m for 1 M KCl at room temperature).

To maximize the signal-to-noise ratio and have a current blockage close to 100%, the pore diameter should match the analyte size. Therefore, direct detection of such small analytes will require ultra-small pores of ~0.12 nm and lower noise levels. However, the fabrication of these pores on SiN membrane remains technically challenging. Embodiments with such ultra-small pores may be fabricated using atomic thin two-dimensional (2D) materials (e.g., graphene and molybdenum disulfide ($MoS_2$)) instead of a SiN membrane. Pores as small as ~0.5 to 1.2 nm can be fabricated with just a few atoms missing on the 2D membrane, which has shown ion selectivity and are useful for water monitoring and desalination. Furthermore, larger pores can be shrunk and coated with atomic-layer-deposited (ALD), sub- to few-nm-thick layers of titanium dioxide ($TiO_2$), aluminum oxide ($Al_2O_3$), and hafnium dioxide ($HfO_2$), which also increases pore lifetime and stability up to months.

Detection of Metal Ions Using Aptamer as the Carrier

As noted above, aptamers may be used as a carrier to enable metal ion detection by forming the specific aptamer-metal ion complex. Upon binding metal ions, the aptamer will display different properties (e.g., structure change), which can be sensed and identified by the nanopore measurement. Generally, aptamers are short, single-stranded oligonucleotides with high specific affinity to a target. Aptamers also possess the advantages of accuracy, stability, and lack of immunogenicity and toxicity. Aptamers can be synthesized and easily modified (e.g., sequences and lengths) to recognize, fold into unique conformation, and envelop the targets. With regard to the detection of heavy metal ions, several DNA aptamers have been developed mainly for $Hg^{2+}$, $Pb^{2+}$, silver ($Ag^+$), cadmium ($Cd^{2+}$) and arsenic ($As^{3+}$) ions. Metal ions can specifically interact with selective bases of DNA to form strong and stable complexes. The techniques described herein will help identify analytes of similar physicochemical properties. Different analytes will have unique electrical signals due to their size, physicochemical properties, and interactions with the pore. Analytes are intercepted within the nanopore and the measured current is reduced as they pass and occlude the pore.

Figures 5A, 5B:
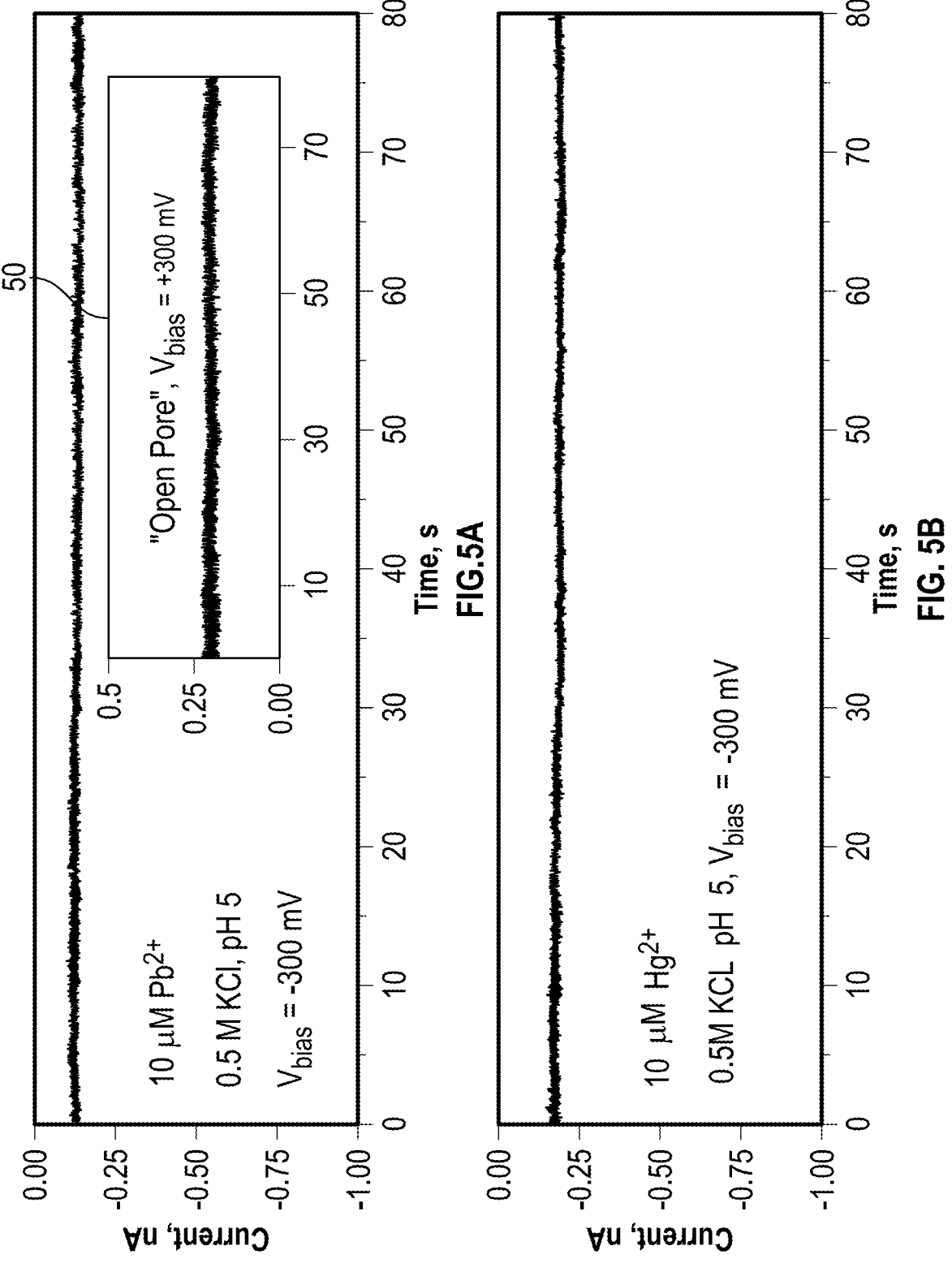
FIG. 5A is a graph showing ionic current (nA) through the nanopore vs. time(s) traces recorded when $Pb^{2+}$ is added into 0.5 M KCl, pH 5 at V=−300 mV to generate a flat control current signal baseline ("open pore") of the same pore without any molecules added.
FIG. 5B is a graph showing ionic current (nA) through the nanopore vs. time(s) traces recorded when $Hg^{2+}$ is added into 0.5 M KCl. pH 5 at V=−300 mV to generate a flat control current signal baseline ("open pore") of the same pore without any molecules added.

FIG. 5A is a graph showing ionic current (nA) through the nanopore vs. time(s) traces recorded when $Pb^{2+}$ is added into 0.5 M KCl, pH 5 at V=−300 mV to generate a flat control current signal baseline ("open pore") of the same pore without any molecules added, while FIG. 5B is a graph showing ionic current (nA) through the nanopore vs. time(s) traces recorded when $Hg^{2+}$ is added into 0.5 M KCl, pH 5 at V=−300 mV to generate a flat control current signal baseline ("open pore") of the same pore without any molecules added. The inset 50 in FIG. 5A further shows a flat control current signal baseline ("open pore") of the same pore without any molecules added. From these diagrams, it appears that these small-diameter pores may be too large to directly detect any metal ions as the $I_{rms}$ noise is ~0.01 nA. To attempt the recognition of any events from metal ions only, a simple thresholding at multiples of $$\sigma = I_{baseline}^{rms}$$

was performed and a thresholding of 5σ was chosen to reduce the false events during data recording.

Detection of Lead Ions

As described above with respect to FIG. 2, aptamers which are guanine (G) enriched are known to form G-quadruplex structures in the presence of $Pb^{2+}$, which can be distinguished from aptamer themselves as described with respect to FIG. 3. The passage of aptamers through the pore causes a reduction of the current and the real time current traces provide a control signal.

Figures 6A, 6B:
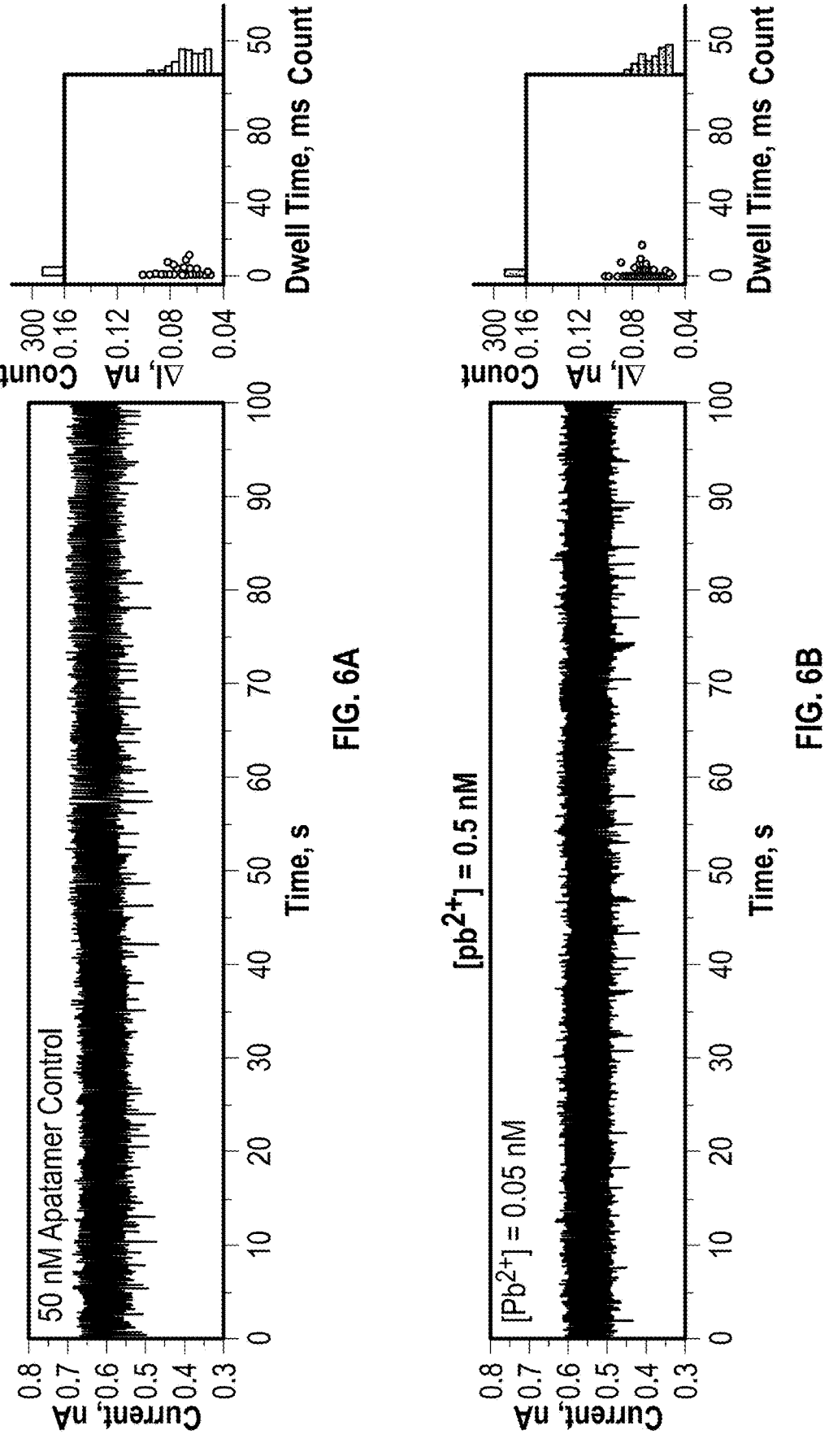
FIGS. 6A-6F are respective graphs showing ionic current (nA) vs. time traces for translocations (left column), blocked current (ΔI) and event duration (dwell time) histograms (right column) of the lead-specific aptamer in the absence (FIG. 6A) and presence (FIGS. 6B-6F) of various lead ions in 0.5 M KCl, pH 5.
Figures 6C, 6D:
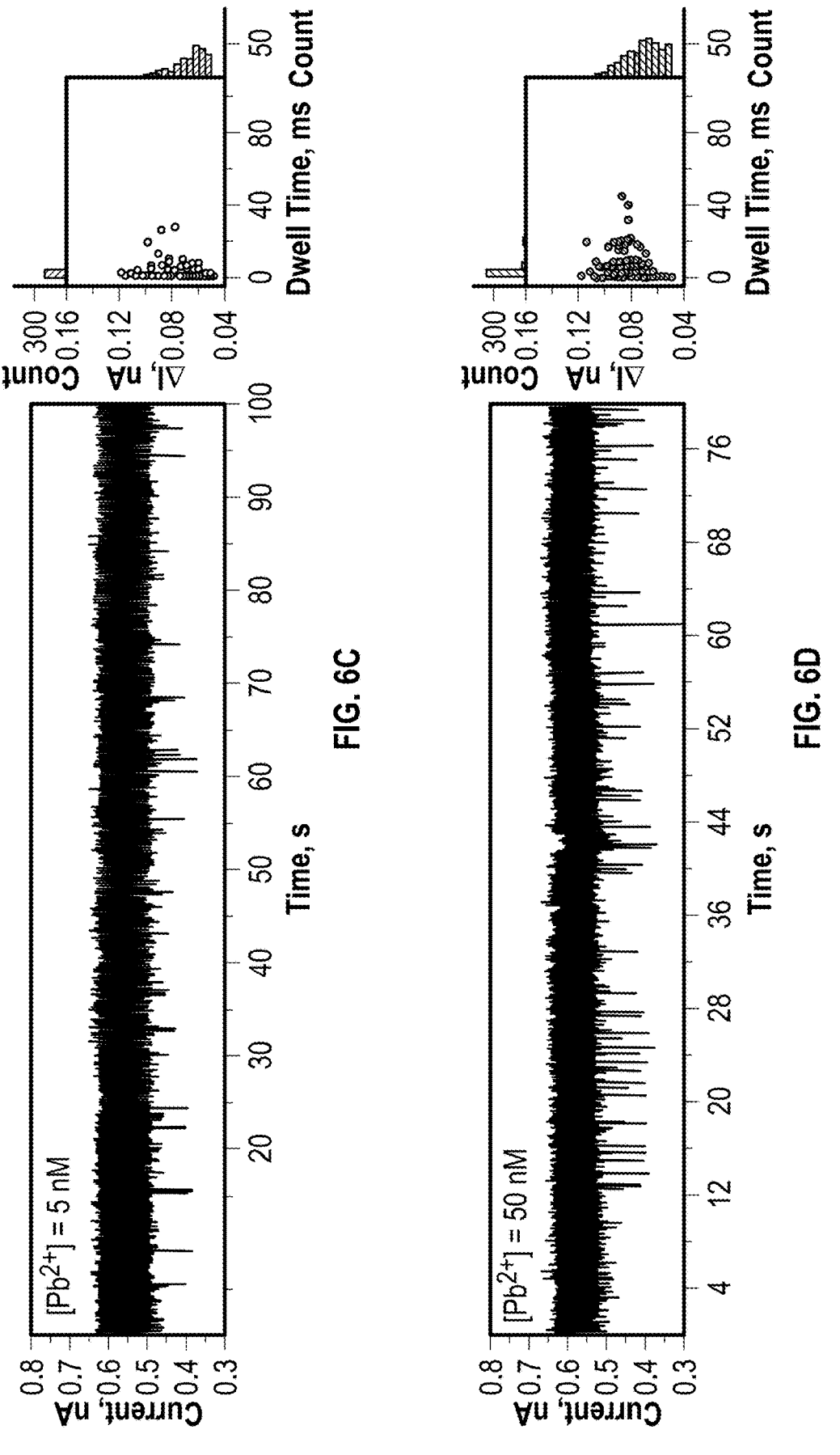
Figures 6E, 6F:
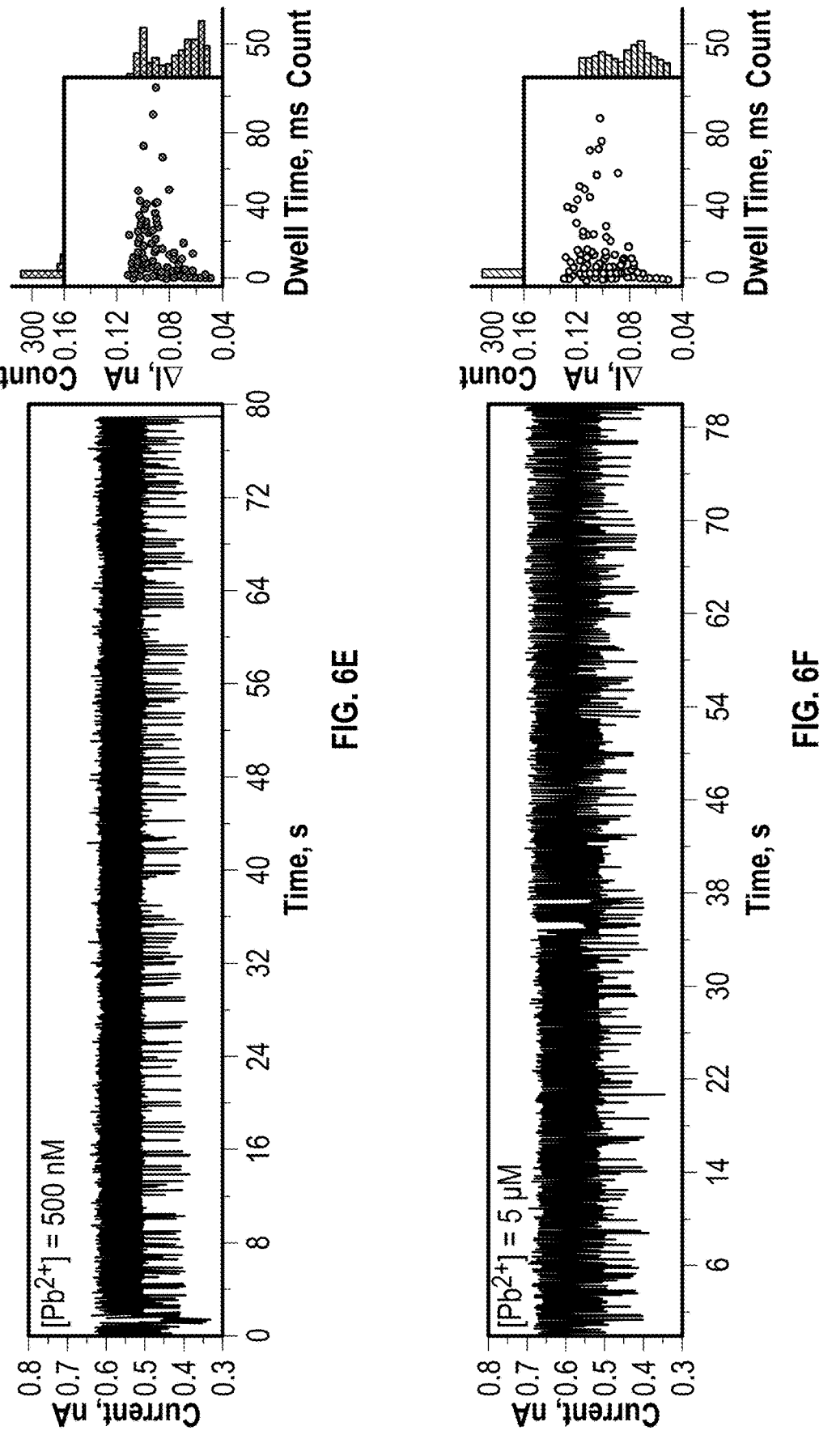

FIG. 6 shows the current traces of aptamers with and without $Pb^{2+}$ using a 3.6 nm diameter pore, which is larger than the aptamer size of ~1.1-1.3 nm. FIGS. 6A-6F are respective graphs showing ionic current (nA) vs. time traces for translocations (left column), blocked current (ΔI) and event duration (dwell time) histograms (right column) of the lead-specific aptamer in the absence (FIG. 6A) and presence (FIGS. 6B-6F) of various lead ions in 0.5 M KCl, pH 5. Data was collected at +200 mV with the nanopore reader 18 (FIG. 1D) at a measurement bandwidth of 20 kHz. Current vs. time traces were analyzed using pClampfit software. The $I_{rms}$ noise was found to be ~0.01 nA. To attempt the recognition of any events from aptamer-metal ion complex, a simple thresholding was performed at multiples of $$\sigma = I_{baseline}^{rms}$$

and a thresholding of 5σ was chosen to reduce the false events during data recording.

From the histograms (right column) of blocked current (ΔI, magnitude of the ionic current reduction) from translocation events (left column), the Gaussian function fitting may be applied to obtain the mean peak values of W/shown in Table 1 below. These peak values and Equation (1) may be used to estimate the average cross-section diameter, $d_{particle}$, of the translocating particles. For example, in the control experiment with aptamer only (FIG. 6A), a mean blocked current peak of 0.054 nA is obtained, and a corresponding $d_{particle}$ of ~1.1 nm (Table 1) is obtained, which is similar to the diameter of an aptamer as expected.

The aptamers (at a fixed concentration of 50 nM) were then mixed with different concentrations of $Pb^{2+}$ and loaded to the same pore. In the presence of $Pb^{2+}$, concentration-dependent translocation characteristics were observed, especially in the average ΔI. At the lowest concentration 0.5 nM $Pb^{2+}$ (FIG. 6B), the estimated $d_{particle}$ was slightly increased to 1.1 nm (Table 1). At a higher concentration of 5 nM (FIG. 6C), translocation events with longer dwell time (>10 ms) and higher average current blockage (~0.10-0.12 nA) than aptamer only were successfully detected, which can be attributed to the formation of aptamer-$Pb^{2+}$ complex. However, the average estimated $d_{particle}$ was only slightly increased to 1.2 nm, indicating the majority of the events are dominated by aptamers without $Pb^{2+}$ binding when $Pb^{2+}$ is at low concentrations. Similar observations become more obvious at $Pb^{2+}$ of 50 nM (FIG. 6D). This suggests the formation and translocation of an increased number of aptamer-$Pb^{2+}$ complex through the pore. Furthermore, the Gaussian fitting yielded another average ΔI peak at 0.08 nA and a corresponding $d_{particle}$ of 1.4 nm (Table 1), slightly larger than an aptamer. The longer dwell time (>10 ms) might be a result from the reduced net negative charge of the aptamer neutralized by the positive $Pb^{2+}$. Under the same positive voltage, the aptamer-$Pb^{2+}$ complex would pass through the pore at a slower speed than the aptamer only.

From 500 nM to 5 μM, more events with longer dwell times (up to 100 ms) and higher current blockades (up to 0.15 nA) were observed. At $Pb^{2+}$ of 500 nM (FIG. 6E), a more distinct bimodal distribution of the events is observed-one is centered at a higher ΔI of ~0.12 nA and a corresponding $d_{particle}$ of 1.7 nm, and the other is centered at ~0.06 nA and a corresponding $d_{particle}$ of 1.2 nm which belongs to the aptamer without $Pb^{2+}$ binding. At $Pb^{2+}$ of 5 μM (FIG. 6F), there is an even higher number of events centered at ~0.12 nA and the estimated $d_{particle}$ is approximately 1.7 nm. The observation of more particles passing the pore with larger estimated diameters indicates the possible formation of the G-quadruplex-shaped aptamer-$Pb^{2+}$ complex, which can form from one, two or four DNA strands. Furthermore, the observation of much longer dwell times than in the aptamer-only scenario (up to 100 ms vs. 10 ms in FIG. 6F and FIG. 6A, respectively) indicates some of the aptamers are getting more and more neutralized by $Pb^{2+}$ and slowly electrophoretically driven through the pore.

Figure 7A:
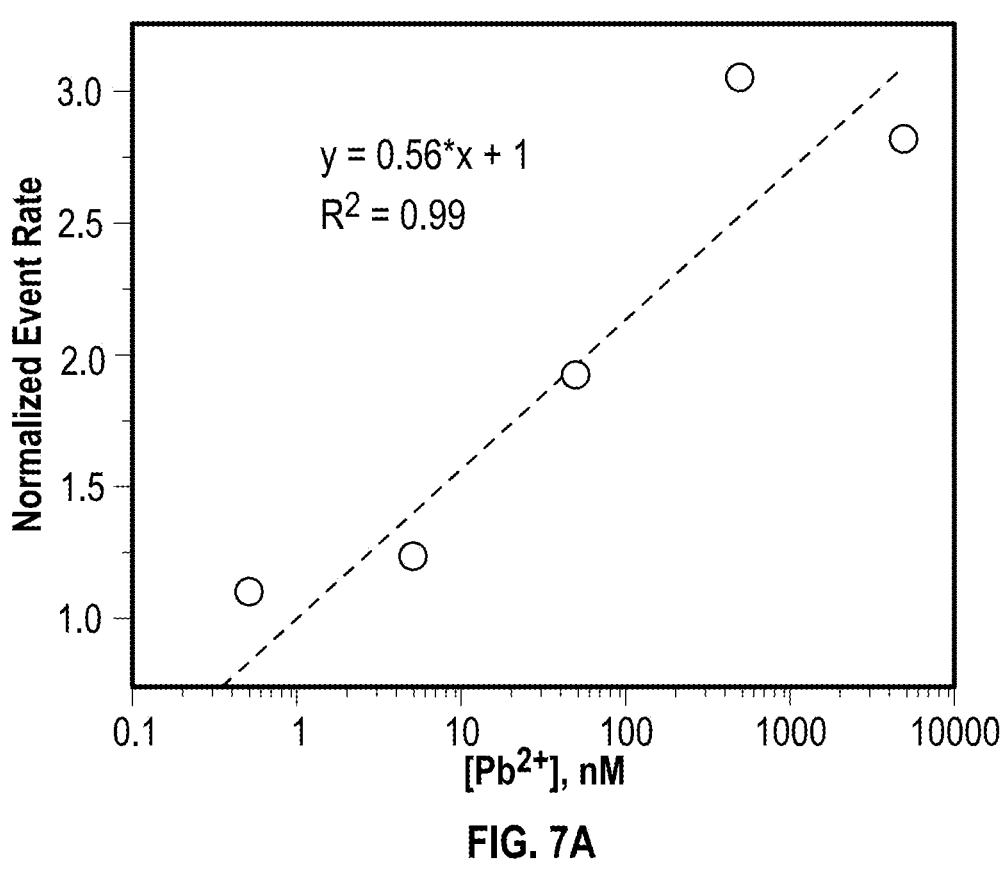
FIG. 7A is a graph showing the event rate (number of events per second) normalized by the value obtained in the absence of $Pb^{2+}$ and plotted as a function of its concentration.

In addition to blocked currents and dwell times, the event rate (number of translocation events per second) is also found to be concentration-dependent. FIG. 7A is a graph showing the event rate (number of events per second) normalized by the value obtained in the absence of $Pb^{2+}$ and plotted as a function of its concentration. It is noted that "1" on the y-axis corresponds to data for aptamer only). As indicated, as the concentration of $Pb^{2+}$ increases, the number of events detected at a fixed duration also increases. At the highest $Pb^{2+}$ of 5 µM, the event rate is almost twice higher than without any $Pb^{2+}$. A linear fitting of the normalized event rate vs. $[Pb^{2+}]$ yields a good correlation with an R-squared value of 0.99. This plot together with the fitted equation may serve as a standard curve to estimate the concentration of $Pb^{2+}$ in unknown water samples.

TABLE 1

Average blocked current (ΔI) peaks and corresponding estimated diameter of translocating particles ($d_{particle}$) obtained from FIG. 6 at various lead ion ($Pb^{2+}$) concentrations.

| $[Pb^{2+}]$, nM | ΔI peak #1, nA | Estimated $d_{particle}$ #1, nm | ΔI peak #2, nA | Estimated $d_{particle}$ #2, nm |
|---|---|---|---|---|
| 0 (control) | 0.054 | 1.1 | | |
| 0.5 | 0.055 | 1.1 | | |
| 5 | 0.062 | 1.2 | | |
| 50 | 0.069 | 1.2 | 0.081 | 1.4 |
| 500 | 0.062 | 1.2 | 0.12 | 1.7 |
| 5000 | 0.073 | 1.3 | 0.11 | 1.6 |

The results clearly indicate that the translocation characteristics of $Pb^{2+}$-specific aptamers in the presence of $Pb^{2+}$ is concentration-dependent. The number of events with high ΔI is expected to continue increasing at higher $Pb^{2+}$ concentrations. The change was detected in the nanopore chip signal (current blockade, dwell time, and event rate) upon the addition of $Pb^{2+}$ at as low as 5 nM (as reflected in the current blockade peak) when using a fixed aptamer of 50 nM. This method has the potential of even lower detection limit if the ratio of aptamer to lead ions is kept the same but the aptamer concentration is decreased. In further embodiments, aptamers with different sequences or various experimental conditions (e.g., pH and electrolyte concentrations) may be used to further improve the detection limit sensitivity, as needed.

Detection of Mercury Ions

As described above with respect to FIG. 4, aptamers that are thymine (T) enriched are known to form a hairpin structure in the presence of $Hg^{2+}$. FIGS. 8A-8F are respective graphs showing ionic current (nA) vs. time traces for translocations (left column), current (I), and event duration (dwell time) histograms (right column) of the mercury-specific aptamer in the absence (FIG. 8A) and presence (FIGS. 8B-8F) of various mercury ions in 0.5 M KCl, pH 5 using a 4.0 nm diameter pore, which is larger than the aptamer size of ~1.1 nm. The $I_{rms}$ noise is ~0.01 nA. To attempt the recognition of any events from aptamer-metal ion complex, a simple thresholding at multiples of $$\sigma = I_{baseline}^{rms}$$

baseline was performed and a thresholding of 5σ was chosen to reduce the false events during data recording. Data was collected at +400 mV with the nanopore reader 18 (FIG. 1D) at a measurement bandwidth of 20 kHz. Current vs. time traces were analyzed using pClampfit software. In the dataset of aptamer-only experiments (FIG. 8A), most translocation events are seen to correspond to a current drop of ~0.1 nA and a corresponding $d_{particle}$ of 1.2 nm (Table 2), similar to the diameter of an aptamer as expected.

The aptamers (at a fixed concentration of 50 nM) were then mixed with different concentrations of $Hg^{2+}$ and loaded to the same pore. In the presence of $Hg^{2+}$, a concentration-dependent translocation characteristic was also observed, especially in the current blockade (ΔI). As the amount of $Hg^{2+}$ increased, more events were observed with higher current blockade, at a concentration as low as 0.5 nM.

Figures 8A, 8B:
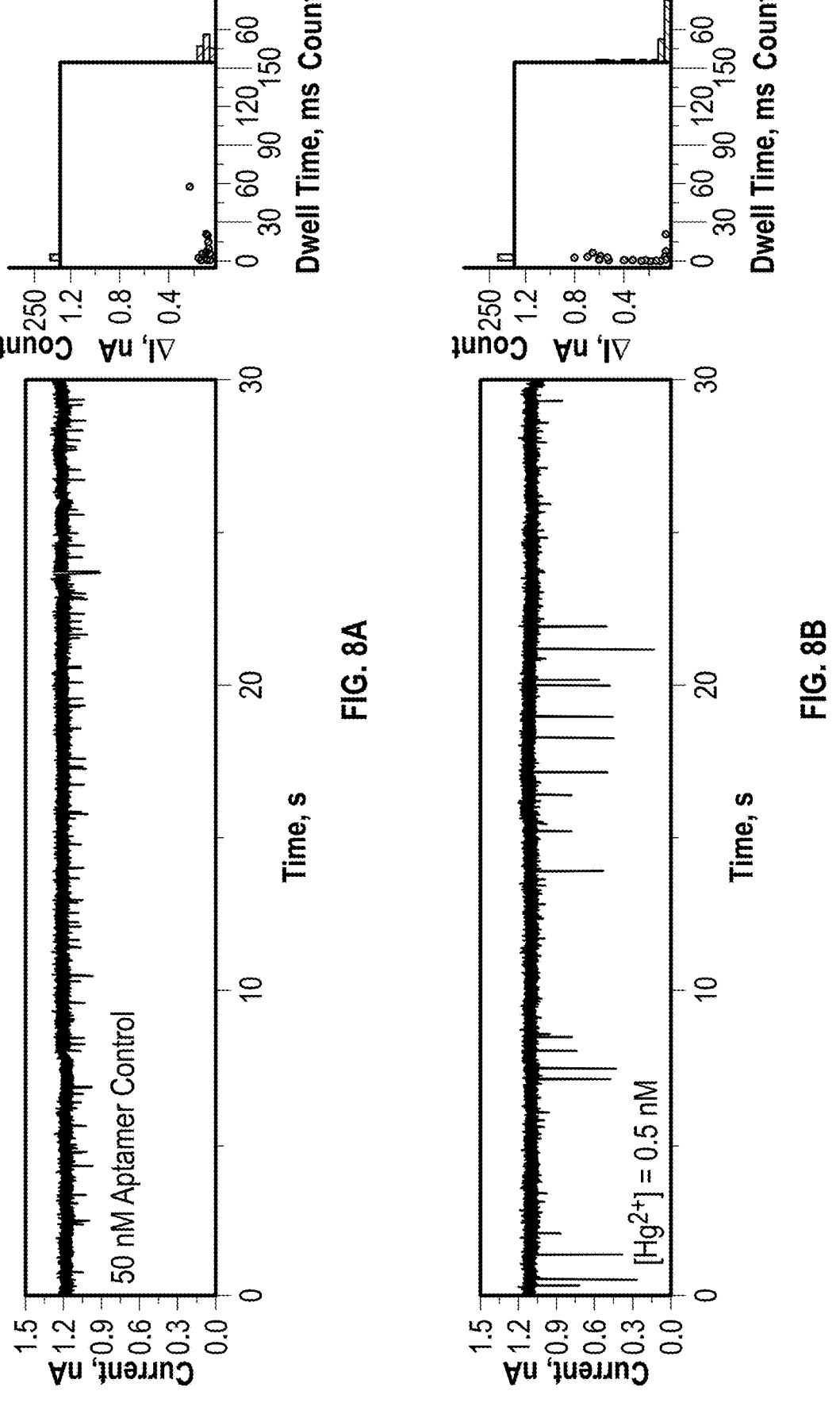
FIGS. 8A-8F are respective graphs showing ionic current (nA) vs. time traces for translocations (left column), current (\), and event duration (dwell time) histograms (right column) of the mercury-specific aptamer in the absence (FIG. 8A) and presence (FIGS. 8B-8F) of various mercury ions in 0.5 M KCl, pH 5.
Figures 8C, 8D:
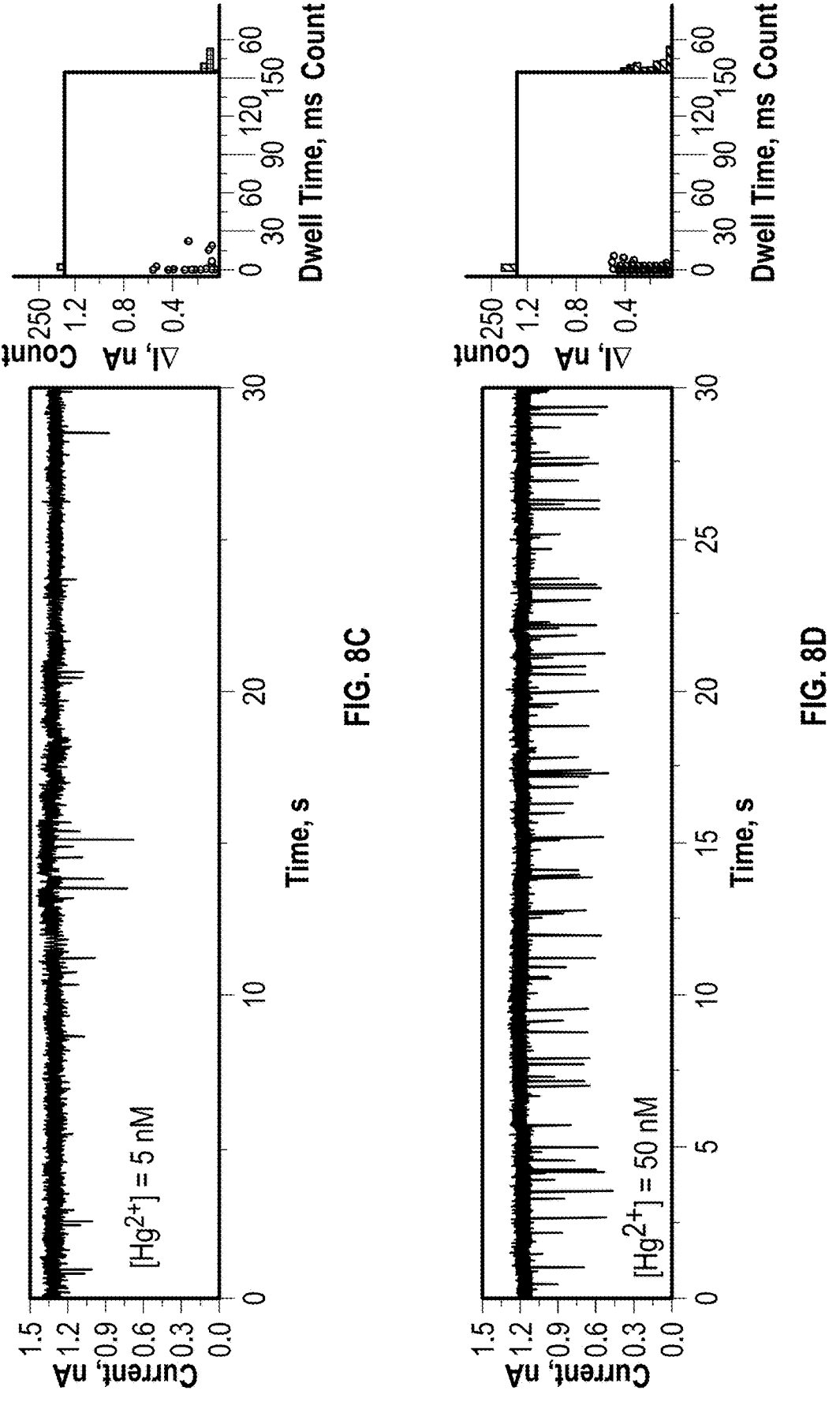

At the lowest concentration of 0.5 nM $Hg^{2+}$ (FIG. 8B), events with higher \ of up to 0.8 nA were observed, which corresponds to an average diameter of up to 3.2 nm for translocating particles. This suggests the formation of the hairpin-shaped aptamer-$Hg^{2+}$ complex and/or intermolecular complexes as the diameter is similar to or slightly larger than that of the double-stranded DNA (dia. ~2.2 nm). However, most events were from aptamers only and the average ΔI was very close to the scenario of the aptamer control sample. Similar trends were observed at the $[Hg^{2+}]$ of 5 nM (FIG. 8C).

Figures 8E, 8F:
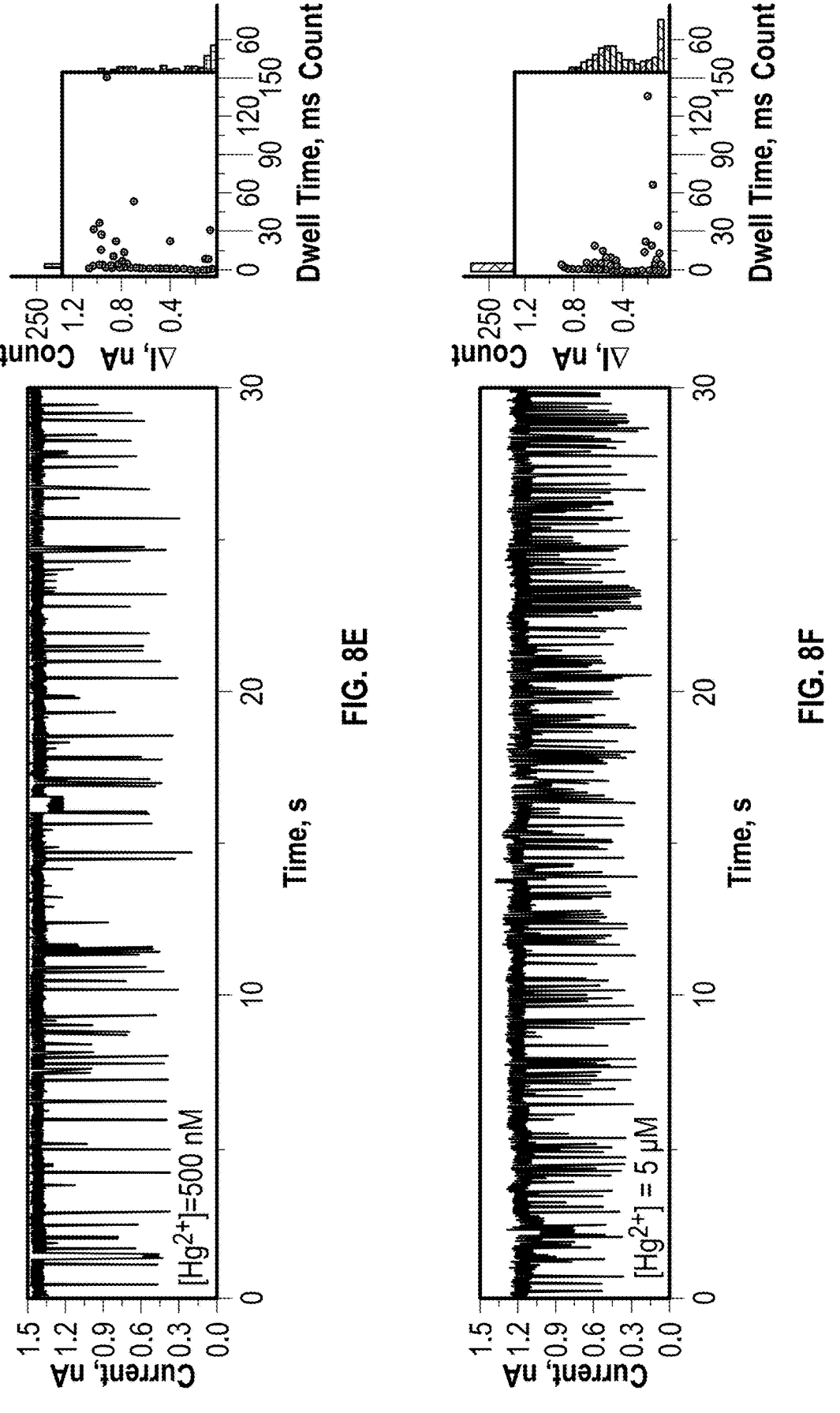

At a higher concentration of 50 nM (FIG. 8D), an increasing number of events were observed with higher ΔI, indicating the formation of more aptamer-$Hg^{2+}$ complexes. By fitting the histogram with Gaussian functions, two blocked current peaks were obtained-one is centered at a higher current blockage of ~0.32 nA and a corresponding $d_{particle}$ of 2.1 nm (Table 2), which can be attributed to the aptamer-$Hg^{2+}$ complex. The other is centered at ~0.11 nA and a corresponding $d_{particle}$ of 1.2 nm, which belongs to the aptamer without $Hg^{2+}$ binding. From 500 nM to 5 µM, an increased number of events were observed with higher current blockade (up to 1 nA in FIG. 8E). At the highest concentration of 5 µM, a more distinct bimodal distribution of the events was observed (FIG. 8F). The estimated $d_{particle}$ at the higher current peak (~2.6 nm, Table 2) is close to the diameter of a double-stranded DNA, which is strong evidence the formation of the hairpin-shaped aptamer-$Hg^{2+}$ complex.

Figure 7B:
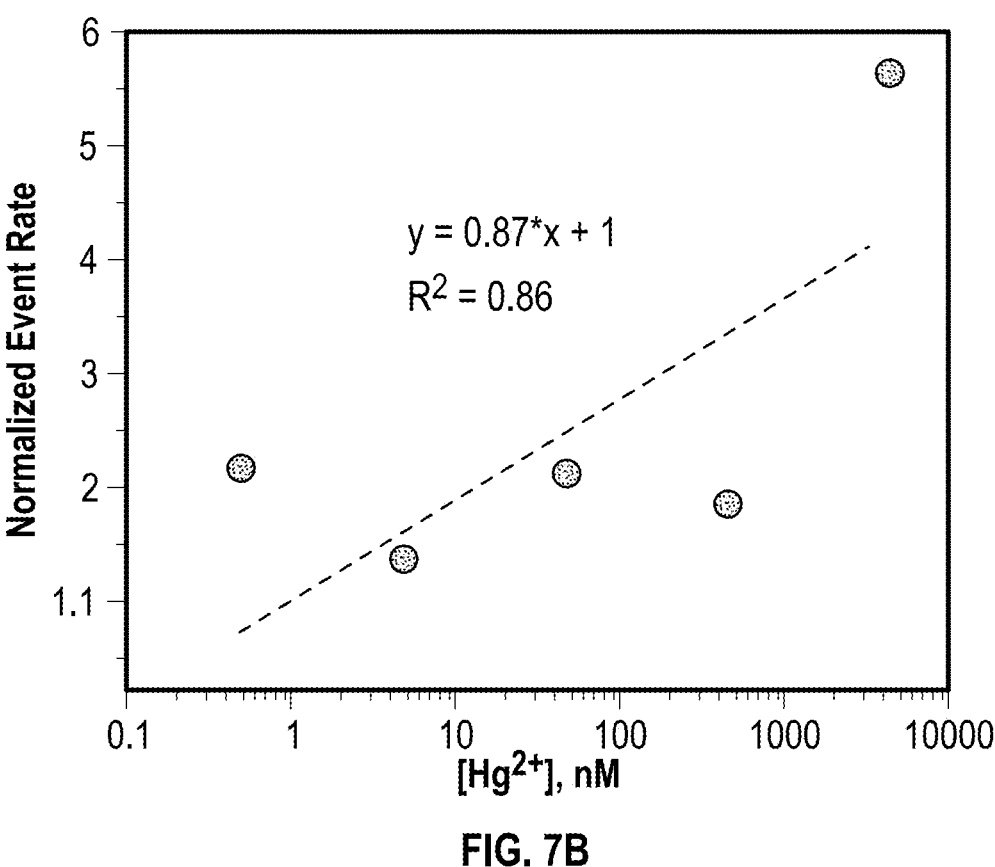
FIG. 7B is a graph showing the event rate (number of events per second) normalized by the value obtained in the absence of $Hg^{2+}$ and plotted as a function of its concentration.

In addition to blocked currents and dwell time, the event rate was also found to be concentration-dependent. FIG. 7B is a graph showing the event rate (number of events per second) normalized by the value obtained in the absence of $Hg^{2+}$ and plotted as a function of its concentration. It is noted that "1" on the y-axis corresponds to data for aptamer only). As the concentration of $Hg^{2+}$ increases, the number of events detected at a fixed duration (30 seconds here) also increases. At the highest $Hg^{2+}$ of 5 µM, the event frequency is almost five times higher than without any $Hg^{2+}$. At the lower concentration from 0.5 to 500 nM, the event rates are almost twice that of the control group despite the lack of significant differences between each concentration. Even though the event rates are close, there is a distinct trend of more events with higher current blockade, indicating the formation of more aptamer-$Hg^{2+}$ complex at higher $Hg^{2+}$ concentrations. This plot together with the fitted equation may serve as a standard curve to estimate the concentration of $Hg^{2+}$ in unknown water samples.

13

TABLE 2

Average blocked current (ΔI) peaks and corresponding estimated diameter of translocating particles ($d_{particle}$) obtained from FIG. 8 at various lead ion ($Hg^{2+}$) concentrations.

| $[Hg^{2+}]$, nM | ΔI peak #1, nA | Estimated $d_{particle}$ #1, nm | ΔI peak #2, nA | Estimated $d_{particle}$ #2, nm |
|---|---|---|---|---|
| 0 (control) | 0.10 | 1.2 | | |
| 0.5 | 0.10 | 1.2 | | |
| 5 | 0.10 | 1.2 | | |
| 50 | 0.11 | 1.2 | 0.32 | 2.1 |
| 500 | 0.10 | 1.1 | 0.48 | 2.3 |
| 5000 | 0.12 | 1.2 | 0.49 | 2.6 |

Similar to the aptamer-assisted $Pb^{2+}$ detection, observations clearly indicate that the translocation characteristics of $Hg^{2+}$-specific aptamers is $Hg^{2+}$ concentration-dependent. The number of events at the higher average blocked current peak is expected to continue increasing at higher $Hg^{2+}$ concentrations. The change in the nanopore chip signal (current blockade, dwell time, and event rate) was detected upon the addition of $Hg^{2+}$ as low as 0.5 nM (as reflected in event rates) when using a fixed aptamer of 50 nM. This method has the potential of even lower detection limit if the ratio of aptamer to lead ion is kept the same but the aptamer concentration is decreased. Further embodiments with different aptamer sequences as well as various experimental conditions (e.g., pH and electrolyte concentrations) may be used to further improve the detection limit sensitivity, as needed.

Enabled by aptamers as a molecular carrier, the solid-state nanopore-based platform of FIG. 1D may be modified to detect selected metal ions ($Hg^{2+}$ and $Pb^{2+}$) in aqueous media. Changes in electrical signal characteristics (reflected in event durations, rates, current magnitudes, and estimated particle diameters) of aptamer-metal ion complex were observed as compared to aptamer only, and differences were observed between the two metal ions. Selective nanopore chips using this platform may identify the characteristic "electrical fingerprints" of these ions. The SiN nanopore platform is capable of sensing the presence of $Hg^{2+}$ and $Pb^{2+}$ at concentrations down to 0.5 nM and 5 nM, respectively, which are below the U.S. EPA maximum contaminant level (MCL) of 25 nM (~2 μg/L) and Spacecraft Water Exposure Guidelines (SWEGs) of 43 nM (~9 μg/L). This platform is portable and enables detection within minutes. The use of aptamer as carriers provides many opportunities and a large library of possible sequences allowing for tuning the carrier-metal ion interactions and nanopore signals, and enabling lower detection sensitivities. Furthermore, the single-molecule nanopore instrument advances the development of new "nanopore kits" for detection of specific metal ions and is thus a promising tool for a miniaturized analytical laboratory for earth-based water monitoring and for future space missions.

It will be understood by one skilled in the art that this disclosure is not limited in its application to the details of construction and the arrangement of components set forth in the description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Although the present disclosure has been described with reference to specific features and embodiments thereof, it is evident that various modifications and combinations can be made thereto without departing from the scope of the disclosure. The specification and drawings are, accordingly, to be regarded simply as an illustration of the disclosure as defined by the appended claims, and are contemplated to cover any and all modifications, variations, combinations or equivalents that fall within the scope of the present disclosure.

What is claimed is:

1. A method of sensing a lead ion in a fluid, comprising:
    inserting a solid-state nanopore chip having at least one nanopore of less than 20 nm diameter into a fluidic cell;
    providing a fluid into the fluidic cell including a guanine (G) rich aptamer that binds with lead ions in the fluid to form lead stabilized G-quadruplex cages; and
    electronically detecting and measuring concentration of the lead stabilized G-quadruplex cages as the fluid passes through the at least one nanopore of the solid-state nanopore chip.

2. The method of claim 1, wherein the solid-state nanopore chip comprises silicon nitride (SiN) nanopores that are less than 20 nm thick and have a diameter of 1.5-5 nm.

3. The method of claim 1, wherein the lead ion has a concentration of 5 nM in the fluid.

4. A method of sensing a mercury ion in a fluid, comprising:
    inserting a solid-state nanopore chip having at least one nanopore of less than 20 nm diameter into a fluidic cell;
    providing a fluid into the fluidic cell including a thymine (T) rich aptamer that binds with mercury ions in the fluid to form a T-Hg-T base pairs in a duplex hairpin structure; and
    electronically detecting and measuring concentration of the T-Hg-T base pairs in the duplex hairpin structure as the fluid passes through the at least one nanopore of the solid-state nanopore chip.

5. The method of claim 4, wherein the mercury ion has a concentration of 0.5 nM in the fluid.

6. The method of claim 1, wherein electronically detecting and measuring the concentration of the lead stabilized G-quadruplex cages comprises recording translocation events of lead stabilized G-quadruplex cages one at a time using a nanopore reader as the lead stabilized G-quadruplex cages translocate through the at least one nanopore.

7. The method of claim 1, wherein the fluid is spacecraft water.

8. A water monitoring system adapted to sense at least one of lead or mercury ions in water, comprising:
    a fluidic cell that holds water comprising a concentration of an at least one of a guanine (G) rich aptamer configured to bind with lead ions in the fluid to form lead stabilized G-quadruplex cages or a thymine (T) rich aptamer configured to bind with mercury ions in the fluid to form a T-Hg-T base pairs in a duplex hairpin structure;
    a solid-state nanopore chip having at least one nanopore of less than 20 nm diameter disposed in the fluidic cell for testing the water; and a nanopore reader configured to detect and measure concentration of at least one of the lead stabilized G-quadruplex cages or the T-Hg-T base pairs in the duplex hairpin structure the carrier as the water passes through the at least one nanopore of the solid-state nanopore chip.

9. The water monitoring system of claim 8, wherein the fluidic cell is disposed on a spacecraft.

10. The water monitoring system of claim 8, wherein the solid-state nanopore chip comprises silicon nitride (SiN) nanopores that are less than 20 nm thick and have a diameter of 1.5-5 nm.

11. The water monitoring system of claim 8, wherein the nanopore reader records translocation events of at least one of lead stabilized G-quadruplex cages or T-Hg-T base pairs in the duplex hairpin structure one at a time as the at least one of lead stabilized G-quadruplex cages or T-Hg-T base pairs in the duplex hairpin structure translocate through the at least one nanopore.

12. The method of claim 4, wherein the solid-state nanopore chip comprises silicon nitride (SiN) nanopores that are less than 20 nm thick and have a diameter of 1.5-5 nm.

13. The method of claim 4, wherein electronically detecting and measuring the concentration of the T-Hg-T base pairs in the duplex hairpin structure comprises recording translocation events of T-Hg-T base pairs in the duplex hairpin structure one at a time using a nanopore reader as the T-Hg-T base pairs in the duplex hairpin structure translocate through the at least one nanopore.

14. The method of claim 4, wherein the fluid is spacecraft water.

\* \* \* \* \*